(12) United States Patent
Warman et al.

(10) Patent No.: US 11,890,481 B2
(45) Date of Patent: *Feb. 6, 2024

(54) AV NODAL STIMULATION DURING ATRIAL TACHYARRHYTHMIA TO PREVENT INAPPROPRIATE THERAPY DELIVERY

(71) Applicant: Medtronic, Inc., Minneapolis, MN (US)

(72) Inventors: Eduardo N. Warman, Maple Grove, MN (US); John E. Burnes, Coon Rapids, MN (US); Koen J. Michels, Maastricht (NL); Paul D. Ziegler, Minneapolis, MN (US); Lillian Kornet, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 668 days.

This patent is subject to a terminal disclaimer.

(21) Appl. No.: 17/035,157

(22) Filed: Sep. 28, 2020

(65) Prior Publication Data
US 2021/0008370 A1   Jan. 14, 2021

Related U.S. Application Data

(63) Continuation of application No. 15/256,091, filed on Sep. 2, 2016, now Pat. No. 10,786,678, which is a
(Continued)

(51) Int. Cl.
*A61N 1/36* (2006.01)
*A61N 1/362* (2006.01)

(52) U.S. Cl.
CPC ......... *A61N 1/3622* (2013.01); *A61N 1/3621* (2013.01); *A61N 1/3624* (2013.01); *A61N 1/36114* (2013.01); *A61N 1/36053* (2013.01)

(58) Field of Classification Search
CPC .............. A61N 1/3622; A61N 1/36114; A61N 1/3621; A61N 1/3624; A61N 1/36053
See application file for complete search history.

(56) References Cited

U.S. PATENT DOCUMENTS 4,951,667 A   8/1990   Markowitz et al.
5,154,170 A   10/1992  Bennett et al.
(Continued)

FOREIGN PATENT DOCUMENTS

CN     101912667 A   12/2010
EP      0547734 A2    6/1993
(Continued)

OTHER PUBLICATIONS

Bianchi et al., "Atrioventricular (AV) Node Vagal Stimulation by Transvenous Permanent Lead Implantation to Modulate AV Node Function: Safety and Feasibility in Humans.," Heart Rhythm, vol. 6, No. 9, Sep. 2009, pp. 1282-1286.
(Continued)

*Primary Examiner* — Rex R Holmes
(74) *Attorney, Agent, or Firm* — Shumaker & Sieffert, P.A.

(57) ABSTRACT

The disclosure describes techniques for delivering electrical stimulation to decrease the ventricular rate response during an atrial tachyarrhythmia, such as atrial fibrillation. AV nodal stimulation is employed during an atrial tachyarrhythmia episode with rapid ventricular conduction to distinguish ventricular tachyarrhythmia from supraventricular tachycardia and thereby prevent delivering inappropriate therapy to a patient.

20 Claims, 9 Drawing Sheets

Related U.S. Application Data continuation of application No. 13/105,689, filed on May 11, 2011, now Pat. No. 9,433,791.

(56) References Cited

U.S. PATENT DOCUMENTS

| | | | |
|---|---|---|---|
| 5,203,326 | A | 4/1993 | Collins |
| 5,243,980 | A | 9/1993 | Mehra |
| 5,320,642 | A | 6/1994 | Scherlag |
| 5,330,507 | A | 7/1994 | Schwartz |
| 5,356,425 | A | 10/1994 | Bardy et al. |
| 5,403,356 | A | 4/1995 | Hill et al. |
| 5,411,531 | A | 5/1995 | Hill et al. |
| 5,507,784 | A | 4/1996 | Hill et al. |
| 5,620,468 | A | 4/1997 | Mongeon et al. |
| 5,683,429 | A | 11/1997 | Mehra |
| 5,855,592 | A | 1/1999 | McGee et al. |
| 5,876,422 | A | 3/1999 | van Groeningen |
| 5,978,700 | A | 11/1999 | Nigam |
| 5,991,656 | A | 11/1999 | Olson et al. |
| 6,256,537 | B1 | 7/2001 | Stoop et al. |
| 6,393,316 | B1 | 5/2002 | Gillberg et al. |
| 6,438,421 | B1 | 8/2002 | Stahmann et al. |
| 6,611,713 | B2 | 8/2003 | Schauerte |
| 6,731,978 | B2 | 4/2004 | Olson et al. |
| 7,139,607 | B1 | 11/2006 | Shelchuk |
| 7,225,019 | B2 | 5/2007 | Jahns et al. |
| 7,245,967 | B1 | 7/2007 | Shelchuk |
| 7,403,819 | B1 | 7/2008 | Shelchuck et al. |
| 8,788,028 | B2 | 7/2014 | Kumar et al. |
| 9,433,791 | B2 * | 9/2016 | Warman .............. A61N 1/3624 |
| 10,786,678 | B2 * | 9/2020 | Warman .............. A61N 1/3622 |
| 2002/0016550 | A1 | 2/2002 | Sweeney et al. |
| 2002/0035335 | A1 | 3/2002 | Scheuerte |
| 2003/0187479 | A1 | 10/2003 | Thong |
| 2005/0119704 | A1 | 6/2005 | Peters et al. |
| 2006/0206159 | A1 | 9/2006 | Moffitt et al. |
| 2006/0224202 | A1 | 10/2006 | Moffitt et al. |
| 2007/0083242 | A1 | 4/2007 | Mazgalev et al. |
| 2007/0197928 | A1 | 8/2007 | Kim et al. |
| 2008/0091240 | A1 | 4/2008 | Ben-David et al. |
| 2008/0269819 | A1 | 10/2008 | Zhou |
| 2009/0182390 | A1 | 7/2009 | Hess |
| 2009/0234408 | A1 | 9/2009 | Moffitt et al. |
| 2010/0036447 | A1 | 2/2010 | Zhang et al. |
| 2011/0004262 | A1 | 1/2011 | Bianchi et al. |

FOREIGN PATENT DOCUMENTS

| | | |
|---|---|---|
| EP | 0756507 A1 | 2/1999 |
| EP | 1426078 A1 | 6/2004 |
| EP | 1870129 A1 | 12/2007 |
| WO | 0071203 A1 | 11/2000 |
| WO | 2007142563 A1 | 12/2007 |
| WO | 2011000558 A1 | 1/2011 |

OTHER PUBLICATIONS

Bianchi et al., "Endocardial Transcatheter Stimulation of the AV Nodal Fat Pad: Stabilization of Rapid Ventricular Rate Response During Atrial Fibrillation in Left Ventricular Failure.," J. Cardiovasc Electrophysiol, vol. 20, No. 1, Jan. 2009, pp. 102-105.

Bianchi et al., "Increase of Ventricular Interval During Atrial Fibrillation by Atrioventricular Node Vagal Stimulation: Chronic Clinical Atrioventricular-Nodal Stimulation Download Study," Circ Arrhythm Electrophysiol, Jun. 2015, pp. 562-568.

Bilgutay et al., Vagal Tuning: A New Concept in the Treatment of Supraventricular Arrhythmias, Angina Pectoris, and Heart Failure, Journal of Thoracic and Cardiovascular Surgery, vol. 56, No. 1, Jul. 1968, pp. 71-82.

Carlsson et al., "Therapy of Atrial Fibrillation: Rythm Control Versus Rate Control," PACE, May 2000; 23: 891-903.

Gal et al. "Effect of Parasympathetic Nerve Stimulation on Atrial and Atrioventricular Nodal Electrophysiological Characteristics," Int J Cardiol., Feb. 15, 2016, pp. 83-85.

Gupta, "Suppression of Paroxysmal Atrial Fibrillation by Pacing," Indian Pacing and Electrophysiology Journal (ISSN 0972-6292), 3(2): 45-46, Apr. 2003.

Harvey et al., "Radiofrequency Catheter Ablation for Atrial Fibrillation," Coronary Artery Disease 1995: 6(2): 115-20. (Applicant points out, in accordance with MPEP 609.04(a), that the year of publication, 1995, is sufficiently earlier than the effective U.S. priority filing date so that the particular month of publication is not in issue.).

Henning et al., "Vagal Nerve Stimulation Increases Right Ventricular Contraction and Relaxation and Heart Rate." Cardiovascular Research 32: 846-853, Nov. 1996.

International Preliminary Report on Patentability from International application No. PCT/US2012/037371 dated Nov. 12, 2013. 8 pp.

International Search Report and Written Opinion from corresponding PCT Application Serial No. PCT/US2012/037371 dated Jan. 2, 2013, 13 pp.

Invitation to pay additional fees from international application No. PCT/US2012/037371, dated Aug. 31, 2012, 6 pp.

Israel et al., "Atrial Pacing in the Prevention of Paroxysmal Atrial Fibrillation: First Results of a New Combined Algorithm," PACE, Nov. 2000; 23 [Pt. II]: 1888-1890.

Kale et al., "Atrial Septal Pacing in Prevention of Paroxysmal Arial Fibrillation Refractory to Antiarrhythmic Drugs," International Journal of Cardiology 82(2): 167-175, Feb. 2002.

Kornet et al., "Stimulation of the Intra-Cardiac Vagal Nerves Innervating the AV-node to Control Ventricular Rate During AF: Specificity, Parameter Optimization and Chronic Use up to 3 Months.," J Interv Card Electrophyiol, Jan. 2012, pp. 7-18.

Levine et al., "Pacing for the Suppression of Paroxysmal Atrial Fibrillation in an 87-year-old Patient," Indian Pacing Electrophysiol, J., Apr. 2003; 3: 88.

Murgatroyd, "Pills and Pulses: Hybrid Therapy for Atrial Fibrillation," J Cardiovasc Electrophysiol vol. 13, pp. S40-S46, Jan. 2002.

Nanthakumar et al., "Inappropriate Therapy From Atrial Fibrillation and Sinus Tachycardia in Automated Implantable Cardioverter Defribillators," Am Heart J., May 2000; 139(5): 797-803.

Notice on the First Office Action from counterpart Chinese Application No. 201280022507.6, dated Oct. 8, 2014, 25 pp.

Notice on the Second Office Action from counterpart Chinese Application No. 201280022507.6, dated Aug. 10, 2015, 8 pp.

Nunain et al., "Limitations and Late Complications of Third-Generation Automatic Cardioverter-Defibrillators," Circulation, Apr. 15, 1995; 91(8): 2204-2213.

Ogawa et al., "Acute Effects of Different Atrial Pacing Sites in Patients with Atrial Fibrillation: Comparison of Single Site and Biatrial Pacing," PACE, Oct. 2001; 24: 1470-78.

Poole et al., "Prognostic Importance of Defibrillator Shocks in Patients with Heart Failure," N Eng J. Med. Sep. 4, 2008; 359 (10) 1009-17.

Purerfellner et al., "Accuracy of Atrial Tachyarrhythmia Detection in Implantable Devices with Arrhythmia Therapies," Pace, Jul. 2004; 27(7): 983-992.

Rosenquist et al., "Relative Importance of Activation Sequence Compared to Atrioventricular Synchrony in Left Ventricular Function," Am J Cardiol, Jan. 15, 1991; 67:148-156.

Rossi et al., "Post-Operative Atrial Fibrillation Management by Selective Epicardial Vagal Fat Pad Stimulation," J Interv Card Electrophysical, Jan. 2009, 24:37-45.

Rossi et al., "Vagal Tone Aumentation to the Atriventricular Node in Humans: Efficacy and Safety of Burst Endocardial Stimulation.," Heart Rhythm, May 2010, pp. 683-689.

Saksena et al., "Prevention of Atrial Fibrillation by Pacing," In Barold SS and Mugica J (Eds), 1998, Recent Advances in Cardiac Pacing: Goals for the 21st Century, Armonk, NY. Futura Publishing Company Inc., pp. 101-114. (Applicant points out, in accordance with MPEP 609.04(a), that the year of publication, 1998, is sufficiently earlier than the effective U.S. priority filing date so that the particular month of publication is not in issue.).

(56) References Cited

OTHER PUBLICATIONS

Schwartz et al., "Long Term Vagal Stimulation in Patients with Advanced Heart Failure: First Experience in Man," Eur J. Heart Fail. Sep. 2008:10(9): 884-91.
The National Heart, Lung, and Blood Institute for Working Group on Atrial Fibrillation: Current Understanding Research Imperatives, J Am Coll Cardiol, Dec. 1993; 22(7): 1830-34.
Tosato et al., "Closed-Loop Control of the Heart Rate by Electrical Stimulation of the Vagus Nerve," Med Biol Eng Comp 44(3): 161-169, Mar. 2006.
Vardas et al, "AAIR Versus DDDR Pacing in Patients with Impaired Sinus Node Chronotropy: An Echocariographic and Cardiopulmonary Study," PACE Jul. 1997; 20: 1762-64.
Wilkoff et al., Critical Analysis of Dual-Chamber Implantable Cardioverter-Defibrilator Arrhythmia Detection: Results and Technical Considerations, Circulation, Jan. 2001, pp. 381-386, vol. 103, No. 3.
Zhang et al., "Chronic Atrioventricular Nodal Vagal Stimulation: First Evidence for Long-Term Ventricular Rate Control in Canine Fibrillation Model," Circulation, Nov. 2005; 112:2904-2911.
Zhang et al., "Optimal Ventricular Rate Slowing During Atrial Fibrillation by Feedback AV Nodal-Selective Vagal Stimulation," Am J Physiol Heart Circ Physiol, Mar. 2002; 282(3):H1102-H1110.
Zhuang et al., "Ventricular Rate Control by Selective Vagal Stimulation is Superior to Rhythm Regularization by Atrioventricular Nodal Ablation and Pacing During Atrial Fibrillation," Circulation, Oct. 2002; 106(14): 1853-1856.
Office Action from U.S. Appl. No. 11/740,565, dated Dec. 30, 2009, 8 pp.
Office Action from U.S. Appl. No. 11/740,565, dated Jan. 21, 2011, 9 pp.
Response to Office Action dated Dec. 30, 2009, from U.S. Appl. No. 11/740,565, filed Apr. 29, 2010, 10 pp.
Response to Office Action dated Jan. 21, 2011, from U.S. Appl. No. 11/740,565, filed Mar. 21, 2011, 8 pp.
Prosecution History from U.S. Appl. No. 13/105,689, from Apr. 25, 2013 through May 6, 2016, 138 pp.
Prosecution History from U.S. Appl. No. 15/256,091, dated Nov. 16, 2016 through Jun. 17, 2020, 110 pp.

\* cited by examiner

AV NODAL STIMULATION DURING ATRIAL TACHYARRHYTHMIA TO PREVENT INAPPROPRIATE THERAPY DELIVERY

This application is a continuation of U.S. patent application Ser. No. 15/256,091 filed Sep. 2, 2016, now U.S. Pat. No. 10,786,678, which is a continuation of U.S. patent application Ser. No. 13/105,689 filed May 11, 2011, now U.S. Pat. No. 9,433,791, the entire content of each application is incorporated herein by reference.

TECHNICAL FIELD

This disclosure relates to medical devices and, more particularly, to medical devices that deliver electrical stimulation therapy.

BACKGROUND

When functioning properly, a heart maintains its own intrinsic rhythm, and is capable of pumping adequate blood throughout a circulatory system. This intrinsic rhythm is a function of intrinsic signals generated by the sinoatrial node, or SA node, located in the upper right atrium. The SA node periodically depolarizes, which in turn causes the atrial heart tissue to depolarize such that right and left atria contract as the depolarization travels through the atrial heart tissue. The atrial depolarization signal is also received by the atrioventricular node, or AV node, which, in turn, triggers a subsequent ventricular depolarization signal that travels through and depolarizes the ventricular heart tissue causing the right and left ventricles to contract.

Some patients, however, have irregular cardiac rhythms, referred to as cardiac arrhythmias. Cardiac arrhythmias result in diminished blood circulation because of diminished cardiac output. Atrial fibrillation is a common cardiac arrhythmia that reduces the pumping efficiency of the heart. Atrial fibrillation is characterized by rapid, irregular, uncoordinated depolarizations of the atria. These depolarizations may not originate from the SA node, but may instead originate from an arrhythmogenic substrate, such as an ectopic focus, within the atrial heart tissue. The reduced pumping efficiency due to atrial fibrillation requires the ventricles to work harder, which is particularly undesirable in sick patients that cannot tolerate additional stresses. As a result of atrial fibrillation, patients must typically limit activity and exercise.

An even more serious problem, however, is the induction of rapid and irregular ventricular heart rhythms by the atrial fibrillation. Irregular atrial depolarization signals associated with atrial fibrillation are received by the AV node and may be conducted to the ventricles. During atrial fibrillation, the intervals between ventricular depolarizations may be shortened and vary substantially. Such induced arrhythmias compromise pumping efficiency even more drastically than atrial arrhythmias. This phenomenon is referred to as rapidly conducted atrial fibrillation, or "conducted AF."

SUMMARY

This disclosure is directed toward delivering AV nodal stimulation to decrease the ventricular rate response to a conducted atrial tachyarrhythmia. AV nodal stimulation is employed during an atrial tachyarrhythmia episode with rapid ventricular conduction to distinguish ventricular tachyarrhythmia from supraventricular tachycardia and thereby prevent delivering inappropriate therapy to a patient.

In one example, a method includes detecting an atrial tachyarrhythmia, during the detected atrial tachyarrhythmia, anticipating detection of a ventricular tachyarrhythmia in a heart of a patient based on a threshold value of a ventricular tachyarrhythmia event count, in response to anticipating detection of the ventricular tachyarrhythmia, delivering electrical stimulation to block the atrioventricular node of the heart, and terminating the delivery of electrical stimulation based on one or more stimulation termination criteria.

In one example, a method includes anticipating detection of a ventricular tachyarrhythmia in a heart of a patient and, in response to anticipating detection of the ventricular tachyarrhythmia, delivering electrical stimulation to block the atrioventricular node of the heart over an electrical stimulation delivery time period. The electrical stimulation is delivered based on a sense time period over which ventricular depolarizations can be sensed during the electrical stimulation delivery time period.

In another example, a system includes a stimulation generator and a processor. The stimulation generator is configured to deliver vagal stimulation to a patient. The processor is configured to anticipate detection of a ventricular tachyarrhythmia in a heart of the patient and, in response to anticipating detection of the ventricular tachyarrhythmia, control the stimulation generator to deliver electrical stimulation to block the atrioventricular node of the heart over an electrical stimulation delivery time period. The processor controls the stimulation generator to deliver the electrical stimulation based on a sense time period over which ventricular depolarizations can be sensed during the electrical stimulation delivery time period.

In another example, a computer-readable storage medium includes instructions for causing a programmable processor to anticipate detection of a ventricular tachyarrhythmia in a heart of a patient and, in response to anticipating detection of the ventricular tachyarrhythmia, deliver electrical stimulation to block the atrioventricular node of the heart over an electrical stimulation delivery time period. The electrical stimulation is delivered based on a sense time period over which ventricular depolarizations can be sensed during the electrical stimulation delivery time period.

In another example, a system includes means for anticipating detection of a ventricular tachyarrhythmia in a heart of a patient and means for, in response to anticipating detection of the ventricular tachyarrhythmia, delivering electrical stimulation to block the atrioventricular node of the heart over an electrical stimulation delivery time period. The electrical stimulation is delivered based on a sense time period over which ventricular depolarizations can be sensed during the electrical stimulation delivery time period.

In another example, a method includes anticipating a ventricular tachyarrhythmia in a heart of a patient and, in response to anticipating the ventricular tachyarrhythmia, delivering electrical stimulation to block the atrioventricular node of the heart over an electrical stimulation delivery time period. The electrical stimulation is delivered based on a sense time period over which ventricular depolarizations can be sensed during the electrical stimulation delivery time period.

The details of one or more examples are set forth in the accompanying drawings and the description below. Other features, objects, and advantages will be apparent from the description and drawings, and from the claims.

DETAILED DESCRIPTION

Figure 1:
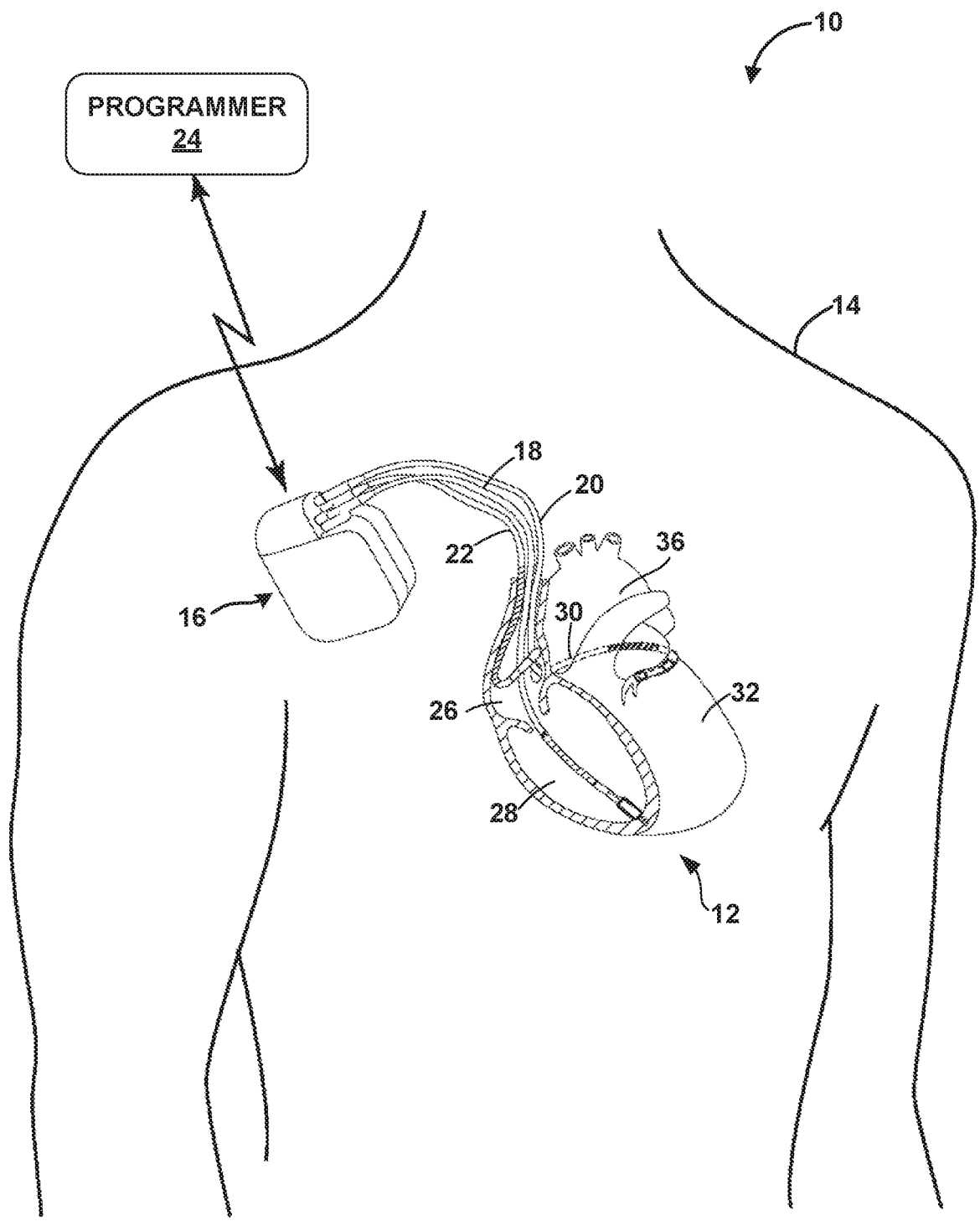
FIG. 1 is a conceptual diagram illustrating an example therapy system comprising an implantable medical device (IMD) that may be used to monitor one or more physiological parameters of a patient and/or provide therapy to the heart of a patient.

This disclosure is directed toward delivering electrical stimulation, e.g., vagal stimulation, to regulate the atrioventricular node (AV node) of the heart of a patient. The electrical stimulation may block conduction of depolarizations to the ventricles via the AV node, but, in general, may include any stimulation that modifies conduction of the AV node. Vagal stimulation, for example, may regulate the cardiac autonomic nervous system by increasing parasympathetic activity in order to reduce the ventricular rate response to a conducted atrial tachyarrhythmia by blocking atrial signals from propagating to the ventricles through the AV node. The electrical stimulation may be employed during an atrial tachyarrhythmia episode with rapid ventricular conduction to distinguish ventricular tachyarrhythmia from supraventricular tachycardia and prevent delivering inappropriate therapy to a patient, e.g., delivering a high voltage shock in response to an incorrectly diagnosed ventricular tachyarrhythmia. An atrial tachyarrhythmia includes, e.g., atrial fibrillation and atrial tachycardia. Similarly, a ventricular tachyarrhythmia includes, e.g., ventricular fibrillation and ventricular tachycardia.

Due to the close relation of vagal innervation to the AV node, high frequency stimulation, e.g., in the form of bursts of pulses or a continuous train of pulses, of the AV node and/or neural fibers proximate to the AV node may provide vagal stimulation appropriate for the examples described herein. Hereinafter, vagal stimulation will be primarily described with respect to the example of AV nodal stimulation. However, in other examples, vagal stimulation may be delivered at other locations including, e.g., epicardially at one or more fat pads, or directly to the vagus nerve via, for example, a cuff electrode. Additionally, as noted above, although vagal stimulation is described in some examples below as the mechanism for regulating conduction of the AV node, in other examples according to this disclosure, other neurological structures that directly or indirectly innervate the AV node may be stimulated.

Under certain circumstances, medical devices that treat cardiac arrhythmias may incorrectly diagnose the arrhythmia and deliver an inappropriate therapy to a patient in response thereto. In one example, an incorrect diagnosis and inappropriate therapy delivery may arise when a medical device misinterprets an atrial tachyarrhythmia with rapid ventricular conduction as a more serious ventricular tachyarrhythmia. The medical device detects the rapid rate response of the ventricle during the atrial tachyarrhythmia and interprets the increased contraction rate as a ventricular tachyarrhythmia instead of a supraventricular tachycardia. In response to the incorrectly detected ventricular tachyarrhythmia, the device delivers an inappropriate therapy to the patient in the form of, e.g., a high voltage shock.

Techniques are disclosed herein that distinguish between ventricular tachyarrhythmia and supraventricular tachycardia, e.g. atrial tachyarrhythmia with rapid ventricular rate response by delivering electrical stimulation, e.g. vagal stimulation, to block the AV node and thereby slow the ventricular rate to unmask the detected ventricular tachyarrhythmia as a supraventricular tachycardia. Additionally, if the AV-node block is not effective in slowing the ventricular rate, then a ventricular tachyarrhythmia episode may be occurring and the device may deliver appropriate therapy, e.g. a high voltage shock to the patient to treat the arrhythmia.

FIG. 1 is a conceptual diagram illustrating an example system 10 that may be used to monitor one or more physiological parameters of patient 14 and/or to provide therapy to heart 12 of patient 14. System 10 includes an implantable medical device (IMD) 16, which is coupled to leads 18, 20, and 22, and programmer 24. IMD 16 may be an implantable pacemaker that provides electrical signals to heart 12 via electrodes coupled to one or more of leads 18, 20, and 22. In addition to pacing therapy, IMD 16 may deliver AV nodal stimulation and/or neurostimulation signals. In some examples, IMD 16 may also include cardioversion and/or defibrillation functionalities. Patient 14 is ordinarily, but not necessarily, a human patient.

Leads 18, 20, 22 extend into the heart 12 of patient 14 to sense electrical activity of and/or deliver electrical stimulation to the heart. In the example shown in FIG. 1, right ventricular (RV) lead 18 extends through one or more veins (not shown), the superior vena cava (not shown), and right atrium 26, and into right ventricle 28. RV lead 18 may be used to deliver RV pacing to heart 12. Left ventricular (LV) lead 20 extends through one or more veins, the vena cava, right atrium 26, and into the coronary sinus 30 to a region adjacent to the free wall of left ventricle 32 of heart 12. LV lead 20 may be used to deliver LV pacing to heart 12.

In some examples, LV lead 20 may be used in combination with RV lead 18 to deliver biventricular pacing to heart 12, which may provide cardiac resynchronization therapy (CRT) to heart 12. CRT may be used to treat heart failure-inducted conduction disturbances and/or ventricular dyssynchrony. In some cases, CRT may help restore the mechanical sequence of ventricular activation and contraction. Additionally, CRT may involve biventricular pacing, e.g., via RV lead 18 and LV lead 20, to synchronize the contraction of both ventricles. In other examples, CRT may involve pacing one of the ventricles, e.g., LV 32 via LV lead 20, to synchronize its contraction with that of the other ventricle.

Right atrial (RA) lead 22 extends through one or more veins and the vena cava, and into the right atrium 26 of heart 12. RA lead 22 may be positioned in the inferior portion of right atrium 26. In some examples, RA lead 22 may be positioned in the posterior portion of right atrium 26 around the coronary sinus ostium, such as posteriorly to the coronary sinus ostium, and along the septum that separates right atrium 26 and left atrium 36. For example, RA lead 22 may be positioned such that RA lead 22 may sense electrical activity within right atrium 26, pace right atrium 26, and also deliver a stimulation signal to or proximate to the AV node, e.g., to or proximate to the AV nodal vagal fat pad.

In some examples, system 10 may include an additional lead or lead segment (not shown in FIG. 1) that deploys one or more electrodes within the vena cava or other vein, or within or near the aorta. In other examples, system 10 may include one or more additional intravenous or extravascular leads or lead segments that deploy one or more electrodes epicardially, e.g., near an epicardial fat pad, or proximate to the vagal nerve. In other examples, system 10 need not include one of ventricular leads 18 and 20, such as where CRT is provided by pacing one ventricle, rather than both ventricles.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar.

IMD 16 may trigger ventricular pacing, e.g., RV, LV, or biventricular pacing, based on atrial depolarizations sensed via RA lead 22. As another example, RA lead 22 may deliver atrial pacing, and IMD 16 may trigger ventricular pacing based on atrial-paced events. In some examples, RV lead 18 and/or LV lead 20 may sense ventricular depolarizations, and IMD 16 may trigger ventricular pacing, e.g., RV, LV, or biventricular pacing, based on whether RV lead 18 and/or LV lead 20 detects an intrinsic ventricular depolarization within a defined time interval following the atrial sensed or paced event. The time interval between an atrial sensed or paced event and delivery of a pacing pulse to one or more of the ventricles may be referred to as an AV interval.

IMD 16 may also provide neurostimulation therapy, defibrillation therapy and/or cardioversion therapy via electrodes located on at least one of the leads 18, 20, 22. IMD 16 may detect an arrhythmia of heart 12, such as fibrillation of ventricles 28 and 32, and deliver defibrillation therapy to heart 12 in the form of electrical shocks, which may take the form of pulses. In some examples, IMD 16 may be programmed to deliver a progression of therapies, e.g., shocks with increasing energy levels, until a fibrillation of heart 12 is stopped. IMD 16 may detect fibrillation employing one or more appropriate fibrillation detection techniques. IMD 16 may similarly deliver anti-tachycardia pacing or cardioversion in response to detecting tachycardia of ventricles 28 and 32.

The techniques disclosed herein are directed to employing electrical stimulation, e.g. vagal stimulation to block the AV node during an atrial tachyarrhythmia episode with rapid ventricular conduction to distinguish ventricular tachyarrhythmia from supraventricular tachycardia and prevent delivering inappropriate therapy to a patient, e.g., delivering a high voltage shock in response to an incorrectly diagnosed ventricular tachyarrhythmia. For example, IMD 16 may also detect an atrial tachyarrhythmia, such as atrial fibrillation, and deliver AV nodal vagal stimulation to reduce the ventricular rate response to the atrial tachyarrhythmia. In one example, IMD 16 monitors heart 12 of patient 14 for a ventricular tachyarrhythmia using, e.g., one or more electrodes connected to one or more of leads 18, 20 and 22 according to any of a number of appropriate ventricular tachyarrhythmia detection techniques.

In addition to monitoring heart 12 for a ventricular tachyarrhythmia, IMD 16 is configured to detect an atrial tachyarrhythmia employing, e.g., RA lead 22 positioned to sense electrical activity within right atrium 26. In one example, as a threshold to detecting an arrhythmia in heart 12 of patient 14, IMD 16 analyzes the rhythm of heart 12 for indications of sinus tachycardia. Accelerated heart rates commonly indicate conditions for which patient 14 may need therapy, such as an atrial or ventricular tachyarrhythmia. However, rapid heart rates are also caused by normal physiological conditions including, e.g., exercise, stress, and certain emotional responses. Analyzing the rhythm of heart 12 of patient 14 for indications of sinus tachycardia, therefore, provides a confirmation that a treatable arrhythmia versus normal physiological response is occurring in the patient's heart. In one example, IMD 16 may be programmed to determine if the R-R intervals of heart 12 are approximately equal to the P-P intervals, and/or to determine if the R-R intervals and/or P-P intervals are within a set physiological limit for patient 14, all of which may be indicative of a sinus tachycardia, rather than a ventricular tachyarrhythmia.

In some examples, atrial tachyarrhythmia is indicated by more contractions in atria 26, 36 than in ventricles 28, 32 of heart 12. P-P interval is a measure of the length of the depolarization and repolarization cycle of atria 26, 36. Similarly, R-R interval is a measure of the length of the depolarization and repolarization cycle of ventricles 28, 32. As such, the contraction rate of atria 26, 36 increases as the P-P interval decreases.

IMD 16 may therefore detect an atrial tachyarrhythmia by, e.g., detecting a P-P interval in heart 12 of patient 14 that is less than a percentage threshold of an R-R interval of the heart. In some examples, IMD 16 monitors heart 12 and stores a number of P-P and R-R intervals and compares a median P-P interval to a median R-R interval. The percentage threshold of the R-R interval may be based on empirical data indicating at what differential between the number of atrial and ventricular contractions is an atrial tachyarrhythmia indicated. In one example, IMD 16 detects an atrial tachyarrhythmia when the device detects a median P-P interval that is less than approximately 93.75% of a median R-R interval.

As explained above, in the course of treating patient 14, IMD 16 may incorrectly interpret characteristics of the rhythm of heart 12 that indicate a supraventricular tachycardia as a more serious ventricular tachyarrhythmia, e.g. a potentially life-threatening ventricular fibrillation. One situation in which IMD 16 is susceptible to such confusion arises from rapid ventricular conduction through the AV node during atrial tachyarrhythmia, e.g., atrial fibrillation. In such circumstances, IMD 16 may incorrectly diagnose the rapid contraction rate of ventricles 28, 32 as a ventricular versus supraventricular phenomenon and deliver an inappropriate stimulation therapy to patient 14, such as delivering a high voltage shock to heart 12. In order to mitigate the risk of misdiagnosis and inappropriate therapy delivery based thereon, therefore, IMD 16 may anticipate imminent ventricular tachyarrhythmia detection and take measures, described below, prior to the detection.

In one example, IMD 16 monitors heart 12 for ventricular tachyarrhythmia events, e.g. a threshold ventricular contraction rate and increments a counter upon detection of each such event. IMD 16 may anticipate ventricular tachyarrhythmia detection when the ventricular tachyarrhythmia event count exceeds a threshold value. By anticipating potentially incorrect ventricular tachyarrhythmia detection, IMD 16 is able to intervene with AV nodal stimulation, e.g. vagal stimulation to impede rapid atrioventricular conduction during atrial tachyarrhythmia before the device incorrectly diagnoses and treats patient 14 for a ventricular tachyarrhythmia. In some examples, IMD 16 need not intervene with vagal or another type of electrical stimulation until an imminent detection is indicated with a threshold confidence by basing the anticipation of a ventricular tachyarrhythmia on a number of events indicative of such a condition.

IMD 16 may take one more precautions as a precondition to delivering AV nodal stimulation to heart 12 to reduce the ventricular rate response to an atrial tachyarrhythmia. In some examples, IMD 16 may measure the R-R interval of heart 12 to confirm that the contraction rate of ventricles 28, 32 is in a range appropriate for intervening with AV nodal stimulation. In particular, IMD 16 may determine a median R-R interval from a number of measured R-R intervals for heart 12 to confirm that the contraction rate of ventricles 28, 32 is below a maximum threshold and above a minimum threshold. For example, a supraventricular tachycardia for which AV nodal stimulation may be employed is not likely if the ventricular contraction rate is too fast (i.e. RR median is too low), e.g. if the rate is greater than 240 beats per minute (bpm). Conversely, if the contraction rate of ventricles 28, 32 is too slow (i.e. R-R median too high), the ventricular conduction through the AV node during atrial tachyarrhythmia may not be considered rapid enough to even warrant attention, let alone intervention with AV nodal stimulation.

In one example, IMD 16 may deliver AV nodal stimulation to patient 14 in response to a command from a user, such as patient 14 or a clinician via, e.g. programmer 24. In such examples, user activation of AV nodal stimulation may only be allowed in the event IMD 16 detects atrial or ventricular tachyarrhythmia episode in heart 12 of patient 14.

In some examples, in the event an atrial tachyarrhythmia is detected, and a ventricular tachyarrhythmia is not detected but is anticipated, e.g., based on detection of a number of short ventricular intervals, IMD 16 may deliver AV nodal stimulation to patient 14. In one example, IMD 16 employs one or more electrodes of RA lead 22 to deliver stimulation to or proximate to the AV node, e.g., to or proximate to the AV nodal vagal fat pad. IMD 16 delivers vagal stimulation in the form of bursts of pulses or a continuous train of pulses. The stimulation may be delivered according to one or more programmed stimulation parameters including, e.g., amplitude, pulse width and frequency, as well as the number of pulses within a burst. For example, IMD 16 may deliver vagal stimulation via electrodes on lead 22 with a frequency in a range from approximately 20 Hz to approximately 100 Hz, and amplitude in a range from approximately 0.5 volts to approximately 8 volts. IMD 16 delivers vagal stimulation to patient 14 to block the AV node of heart 12, which may act to reduce the ventricular conduction and contraction rate caused by a supraventricular tachycardia, e.g., during an atrial fibrillation.

IMD 16 may, in some examples, also be programmed with stimulation parameters configured to act as safety precautions to guard against AV nodal stimulation preventing appropriate sensing in ventricles 28, 32. For example, as IMD 16 delivers high frequency stimulation, e.g., in the form of bursts of pulses, blanking periods in which the device does not sense ventricular activity may accumulate. A blanking period is a time period over which IMD 16 "blanks" amplifier(s) that are used for sensing to protect them from the high frequency energy being used to deliver stimulation. In this manner, the blanking period is generally equal to the stimulation time period. In some cases, IMD 16 may be programmed to blank an amplifier for a time period that is nominally longer than the stimulation time period as an extra precaution.

There is a risk, as IMD 16 delivers high frequency stimulation, that the stimulation time periods, and therefore the blanking periods, reach a threshold level beyond which IMD 16 may not be able to detect the development of serious arrhythmias in ventricles 28, 32, e.g. ventricular fibrillation. The stimulation frequency may therefore be bounded by limits that are designed to prevent the accumulation of blanking periods beyond a threshold level. For example, a period of time over which a stimulation burst is delivered by IMD 16 may be based on the contraction frequency in ventricles 28, 32 such that the burst period does not subsume the period between ventricular contractions. In this manner, IMD 16 may base the stimulation burst period on, e.g., a median R-R interval for heart 12. In one example, IMD 16 may limit the stimulation burst period to approximately 50% of a median R-R interval for heart 12 of patient 14 such that between ventricular contractions 50% of the time the stimulation burst is delivered and 50% of the time is retained for sensing the activity of ventricles 28, 32.

In some examples, IMD 16 may also be configured to synchronize the delivery of AV nodal stimulation with a QRS complex of heart 12. In particular, IMD 16 may be configured to deliver, e.g. AV nodal vagal stimulation in a refractory period between depolarization/repolarization cycles. During the refractory period, the stimulation is less likely to depolarize heart 12, and, in particular, ventricles 28, 32. In one example, IMD 16 may also synchronize delivery of AV nodal stimulation with a P-wave, which may act to reduce the likelihood of inducing an AT/AF episode after such an episode terminates.

IMD 16 continues to deliver AV nodal stimulation until one or more stimulation termination criteria are satisfied, at which point the device terminates the stimulation. In one example, the termination criteria includes at least one of expiration of a programmed AV nodal stimulation delivery time period, an accumulation of blanking time periods that exceeds a threshold percentage of a AV nodal stimulation delivery time period, failure to detect a threshold ventricular rate response within a AV nodal stimulation response time period, or detection of a ventricular tachyarrhythmia. IMD 16 may also terminate stimulation in the event normal conduction in atriums 26, 36 of heart 12 is detected.

In some examples, IMD 16 is programmed, e.g. according to a therapy program, to deliver AV nodal stimulation for a specific period of time. The programmed stimulation time period may be set to a value that provides a sufficient amount of time for IMD 16 to test the effectiveness of the stimulation in modulating the ventricular rate response. Additionally, regardless of other termination criteria, the stimulation time period may be set to a value that provides hysteresis such that IMD 16 is not rapidly toggling between turning AV nodal stimulation on and off. In one example, IMD 16 is programmed with a AV nodal stimulation time period in a range from approximately 20 seconds to approximately 30 seconds.

As described above with reference to the parameters by which IMD 16 delivers AV nodal stimulation to patient 14, there is a risk that, as IMD 16 delivers high frequency stimulation bursts, blanking periods will accumulate beyond a threshold such that IMD 16 may not be able to detect ventricular depolarizations associated with the development of a ventricular tachyarrhythmia, e.g. ventricular fibrillation in heart 12 of patient 14. IMD 16 may, therefore, determine an amount of time over which ventricular depolarizations need to be sensed during the delivery of stimulation, and deliver the stimulation based on the determined amount of time. In one example, IMD 16 may monitor delivery of vagal stimulation to block the AV node of heart 12 and the periods of time the device is sensing activity in ventricles 28, 32 during stimulation to ensure that the stimulation burst period, which generally corresponds to the blanking period, does not exceed a threshold percentage of the period between depolarizations of ventricles 28, 32 such that the burst period does not subsume the period between the ventricular contractions. In one example, the threshold percentage is 50% such that, for example, the stimulation burst period for vagal stimulation delivered by IMD 16 does not exceed 50% of a median R-R interval for heart 12 of patient 14.

In one such example, IMD 16 may deliver multiple stimulation bursts or multiple series of pulses for a total vagal stimulation time period of 30 seconds. Over the 30 second vagal stimulation time period, a window of at least 15 seconds in which IMD 16 may sense activity in ventricles 28, 32 is needed. In the event the 50% threshold is exceeded, e.g. IMD 16 only senses activity in heart 12 for 10 seconds of a 30 second period, IMD 16 may terminate delivery of vagal stimulation to patient 14.

In some examples, IMD 16 is programmed to allow the stimulation burst period to exceed a threshold for a period at the beginning of the delivery of AV nodal stimulation. As IMD 16 delivers AV nodal stimulation, e.g. vagal stimulation to heart 12, the contraction rate in ventricles 28, 32 may begin to slow, which may, in turn, increase the R-R interval for heart 12. As the R-R interval increases, the percentage of the interval over which the stimulation is delivered decreases.

However, before the effect of the vagal stimulation is able to slow the contractions of ventricles 28, 32, the stimulation burst period may exceed the threshold. Therefore, without permitting the stimulation burst period to exceed the threshold for a brief period of time, the vagal stimulation delivered by IMD 16 may not have an adequate opportunity to affect the rapid ventricular contraction rate in heart 12. In one example, IMD 16 is configured to permit the stimulation burst period to exceed a threshold percentage of the contraction frequency in ventricles 28, 32 for a time period corresponding to a stimulation response time, as described below.

In addition to AV nodal stimulation time period expiration and blanking period accumulation, IMD 16 may be programmed to terminate the delivery of AV nodal stimulation in the event a minimum ventricular rate response is not observed within a programmed response time period. In one example, IMD 16 may be programmed to terminate, e.g. vagal stimulation if the contraction rate of ventricles 28, 32 does not decrease by a threshold amount within the stimulation response time period. The minimum ventricular rate response may differ from one patient to another and may be set as a relative percentage reduction or as an absolute value rate reduction. In examples in which the minimum rate response is set as an absolute value, the value by which IMD 16 measures rate response may be tiered depending on the observed contraction rate of ventricles 28, 32, i.e. the minimum rate response may be higher for higher ventricular contraction rates and lower for lower ventricular contraction rates.

In one example, IMD 16 is programmed with a vagal stimulation response time period of approximately 10 seconds or in a range of 5 to 10 beats of heart 12. Additionally, IMD 16 is programmed with a minimum rate response approximately equal to a 20% rate reduction from the initial contraction rate of ventricles 28, 32. In another example, IMD 16 is programmed with a minimum rate response approximately equal to 40 bpm for higher initial ventricular contraction rates on the order of 180 bpm or higher, and a minimum rate response approximately equal to 20 bpm for lower initial ventricular contraction rates on the order of 120 bpm or lower.

In some examples, the programmed response time period may depend on activity of the sympathetic system of patient 14. The parasympathetic system response generally has a quick on and off set. The sympathetic system, on the other hand, has a slow on and off set. In case the parasympathetic system is stimulated, a decrease in sympathetic activation may occur, which, if it does occur, will make the AV node response stronger. However, the sympathetic influence may not be noticed immediately. In case there is a strong background sympathetic activity counteracting parasympathetic action, it may take longer for the effect of AV nodal stimulation to become noticeable than if no sympathetic background activity is present. This sympathetic activity background level depends on individual patient conditions/characteristics, e.g. arousal levels, circadian rhythm, health, if the patient is tired, anaethesia, medication, and other factors. In one example, the programmed response time period may be set based on, e.g. an average activation of the sympathetic system of patient 14. In one example, average activation of the sympathetic system of patient 14 may be determined by analyzing the low and high frequency content of the frequency spectrum of the R-R interval during a baseline period of time (e.g. during no AT/AF episodes).

Referring again to FIG. 1, programmer 24 comprises a handheld computing device, computer workstation, or networked computing device. Programmer 24 includes a user interface that presents information to and receives input from a user. It should be noted that the user may also interact with programmer 24 remotely via a networked computing device.

A user, such as a physician, technician, surgeon, electrophysiologist, or other clinician, interacts with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

In one example, a user may retrieve information regarding the rhythm of heart 12, trends therein over time, or arrhythmic episodes from IMD 16 using programmer 24. As another example, the user may use programmer 24 to retrieve information from IMD 16 regarding other sensed physiological parameters of patient 14 or information derived from sensed physiological parameters, such as the ventricular rate response of heart 12 during one or more atrial tachyarrhythmia episodes. As another example, the user may use programmer 24 to retrieve information from IMD 16 regarding the performance or integrity of IMD 16 or other components of system 10, such as leads 18, 20 and 22, or a power source of IMD 16. As another example, the user may interact with programmer 24 to program, e.g., select parameters for, therapies provided by IMD 16, such as AV nodal vagal stimulation and, optionally, cardioversion and/or defibrillation. In one example, the user employs programmer 24 to program IMD 16 with one or more of a threshold ventricular tachyarrhythmia event count, vagal stimulation parameters, and stimulation termination criteria.

IMD 16 and programmer 24 may communicate via wireless communication using a number of appropriate techniques including, e.g., low frequency or radiofrequency (RF) telemetry, but other techniques are also contemplated. In some examples, programmer 24 includes a programming head that may be placed proximate to the patient's body near the IMD 16 implant site in order to improve the quality or security of communication between IMD 16 and programmer 24.

Figure 2:
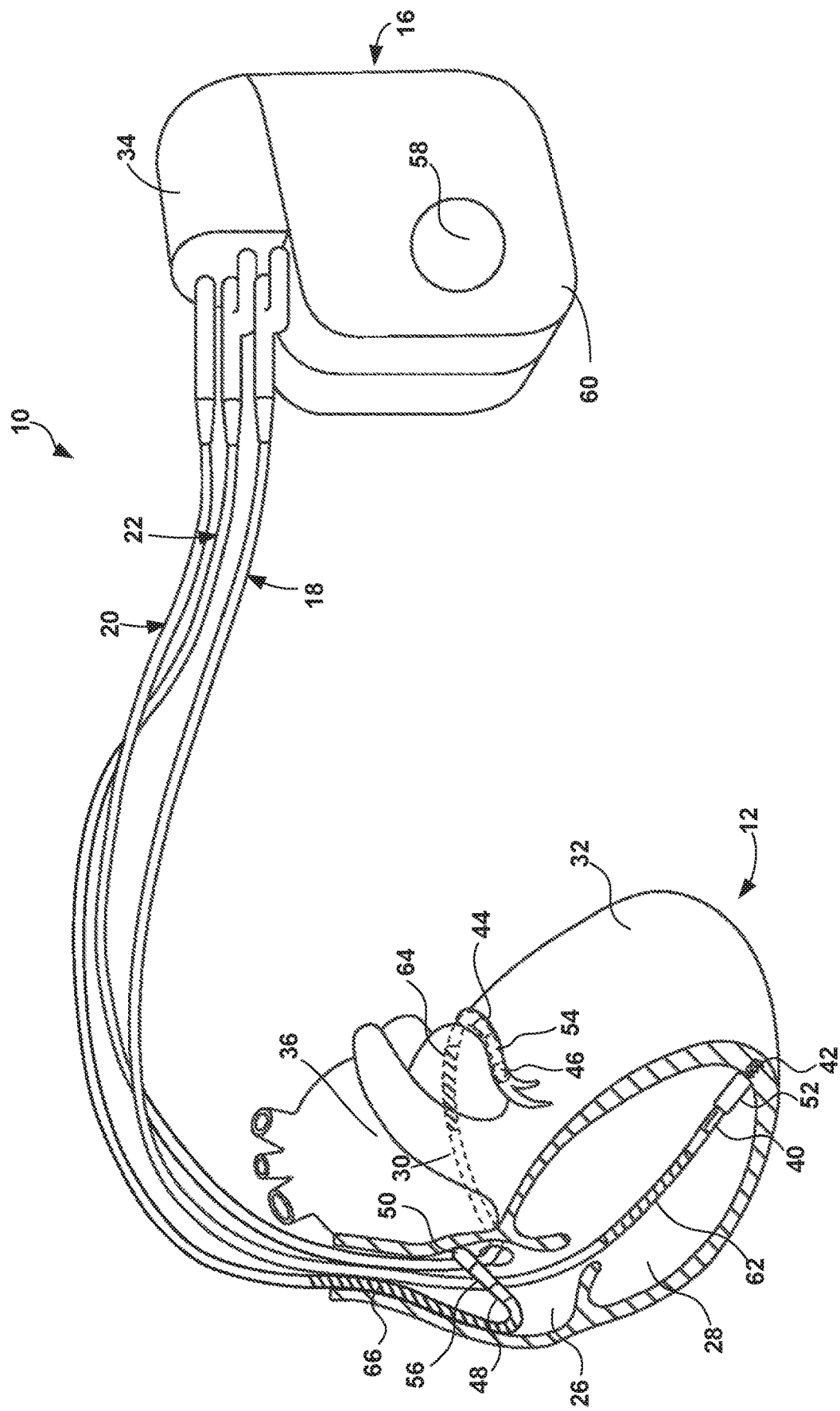
FIG. 2 is a conceptual diagram further illustrating the IMD and leads of the system of FIG. 1 in conjunction with the heart.

FIG. 2 is a conceptual diagram illustrating IMD 16 and leads 18, 20, 22 of therapy system 10 in greater detail. Leads 18, 20, 22 may be electrically coupled to a signal generator and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in left ventricle 32 and bipolar electrodes 48 and 50 are located adjacent to a distal end of lead 22 in right atrium 26.

Electrodes 40, 44, and 48 may take the form of ring electrodes, and electrodes 42, 46, and 50 may take the form of extendable helix tip electrodes mounted retractably within insulative electrode heads 52, 54, and 56, respectively. In some examples, one or more of electrodes 42, 46, and 50 may take the form of pre-exposed helix tip electrodes. In other examples, one or more of electrodes 42, 46, and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64, and 66 may be electrically coupled to a respective one of the coiled conductors within the lead body of its associated lead 18, 20, 22, and thereby coupled to respective ones of the electrical contacts on the proximal end of leads 18, 20, 22.

Helix tip electrode 50, which may be extendable or pre-exposed, of RA lead 22 may be inserted into the tissue of right atrium 26 to substantially fix RA lead 22 within right atrium 26. For example, helix tip electrode 50 may be inserted into or proximate to the endocardium of the septum that separates right atrium 26 and left atrium 36 at a posterior portion of right atrium 26. As described previously, RA lead 22 may be positioned such that RA lead 22 may sense electrical activity within right atrium 26, pace right atrium 26, and also deliver a stimulation signal to (or proximate to) the AV node, e.g., to (or proximate to) the AV nodal vagal fat pad. Helix tip electrode 50 may aid in maintaining RA lead 50 in the appropriate position to provide such functionality.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 3, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 58, 62, 64, and 66. The electrical signals are conducted to IMD 16 from the electrodes via the respective leads 18, 20, 22 or, in the case of housing electrode 58, a conductor coupled to housing electrode 58. IMD 16 may sense such electrical signals via any bipolar combination of electrodes 40, 42, 44, 46, 48, 50, 58, 62, 64, and 66. Furthermore, any of the electrodes 40, 42, 44, 46, 48, 50, 58, 62, 64, and 66 may be used for unipolar sensing in combination with housing electrode 58.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. For example, electrodes 40, 42, and/or 58 may be used to deliver RV pacing to heart 12. Additionally or alternatively, electrodes 44, 46, and/or 58 may be used to deliver LV pacing to heart 12, and electrodes 48, 50 and/or 58 may be used to deliver RA pacing to heart 12. Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

In accordance with the techniques disclosed herein, IMD 16 may also deliver AV nodal stimulation to block the AV node and thereby slow rapid ventricular conduction therethrough during an atrial tachyarrhythmia episode. In one example, IMD 16 delivers AV nodal stimulation to heart 12 via electrodes 48, 50, and/or 66 of RA lead 22, e.g., in a bipolar configuration or in a unipolar configuration in combination with housing electrode 58. For example, IMD 16 may monitor heart 12 for a ventricular tachyarrhythmia, detect an atrial tachyarrhythmia, e.g., via any combination of electrodes 48, 50, 56 and 58, anticipate a ventricular tachyarrhythmia detection, e.g. based on a threshold value of a ventricular tachyarrhythmia event count, and deliver AV nodal stimulation to block the AV node of heart 12. The AV nodal stimulation may reduce the ventricular rate response to the atrial tachyarrhythmia, which in turn will unmask a potentially misdiagnosed ventricular tachyarrhythmia and thereby prevent an inappropriate therapy from being delivered to patient 14. The AV nodal stimulation may include IMD 16 determining an amount of time over which ventricular depolarizations need to be sensed during the delivery of stimulation and delivering the stimulation based on the determined amount of time.

The configuration of system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies, as well as AV nodal stimulation to heart 12 via percutaneous leads that extend through the skin of patient 14 to a variety of positions within or outside of heart 12.

In addition, in other examples, a system may include any suitable number of leads coupled to IMD 16, and each of the leads may extend to any location within or proximate to heart 12. For example, other examples of systems may include three transvenous leads located as illustrated in FIGS. 1 and 2, and an additional lead located within or proximate to left atrium 36. As another example, other examples of therapy systems may include a single lead that extends from IMD 16 into right atrium 26 or right ventricle 28, or two leads that extend into a respective one of the right ventricle 26 and right atrium 26.

Figure 3:
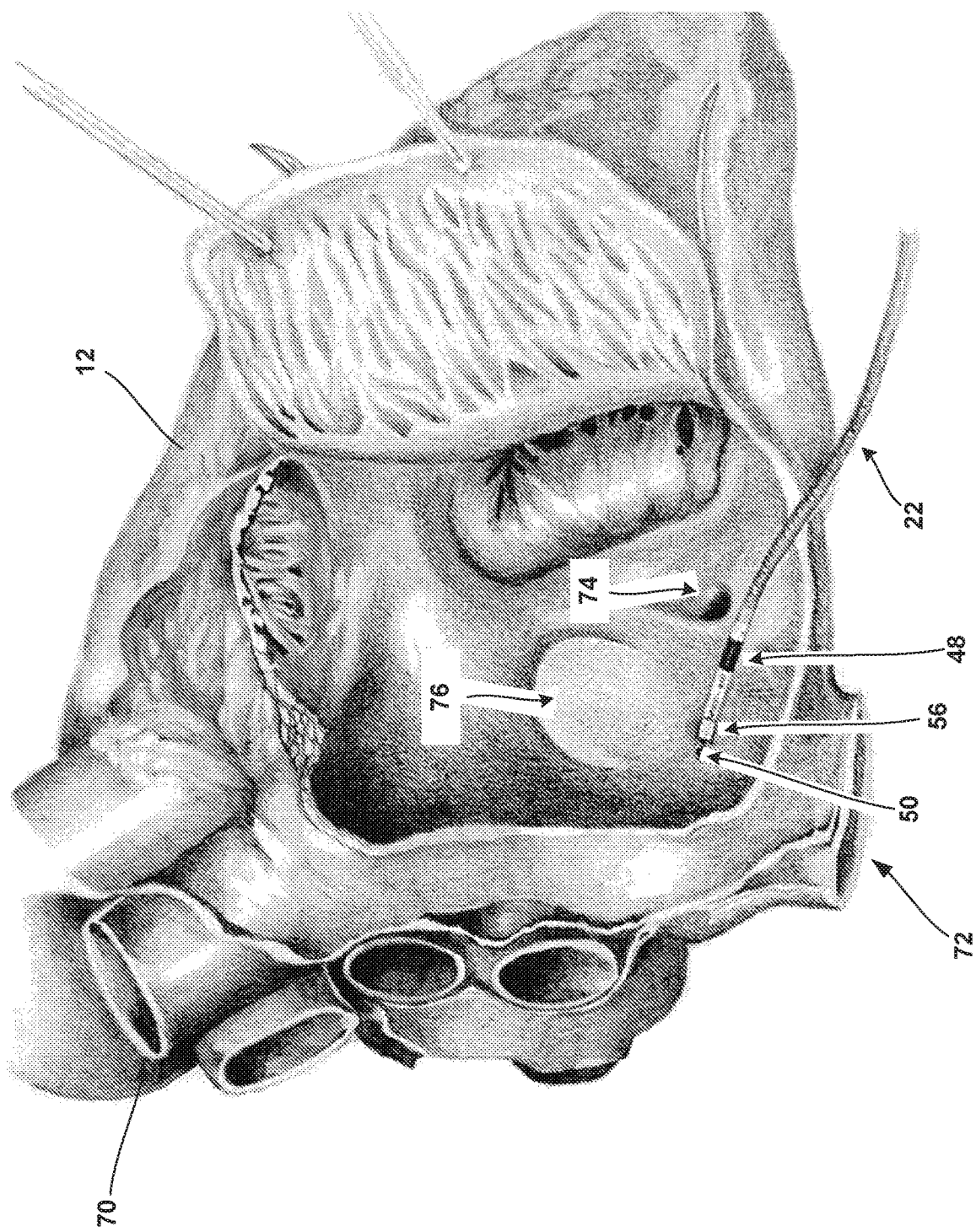
FIG. 3 is a conceptual diagram illustrating an example implantation location for a right atrial lead through which AV nodal vagal stimulation may be delivered.

FIG. 3 is a conceptual diagram illustrating an example implantation location for RA lead 22, through which AV nodal stimulation may be delivered. FIG. 3 illustrates heart 12 with right atrium 26 exposed by dissection and retraction of outer wall of the right atrium. Although not illustrated in FIG. 3, the distal portion of RA lead 22 will generally be advanced to its implantation location within right atrium 26 intravenously and through superior vena cava 70 (or, in some cases, inferior vena cava 72). In the illustrated example, the distal portion of RA lead 22 is positioned and implanted in the posterior portion of right atrium 26, posterior to the coronary sinus ostium 74 and along the septum 76 that separates right atrium 26 and left atrium 36. In one example, the distal portion of RA lead 22 may be positioned and implanted inferior to the coronary sinus ostium 74. Helical tip electrode 50 may engage the endocardial tissue to fix the distal portion lead 22 at this position.

Figure 4:
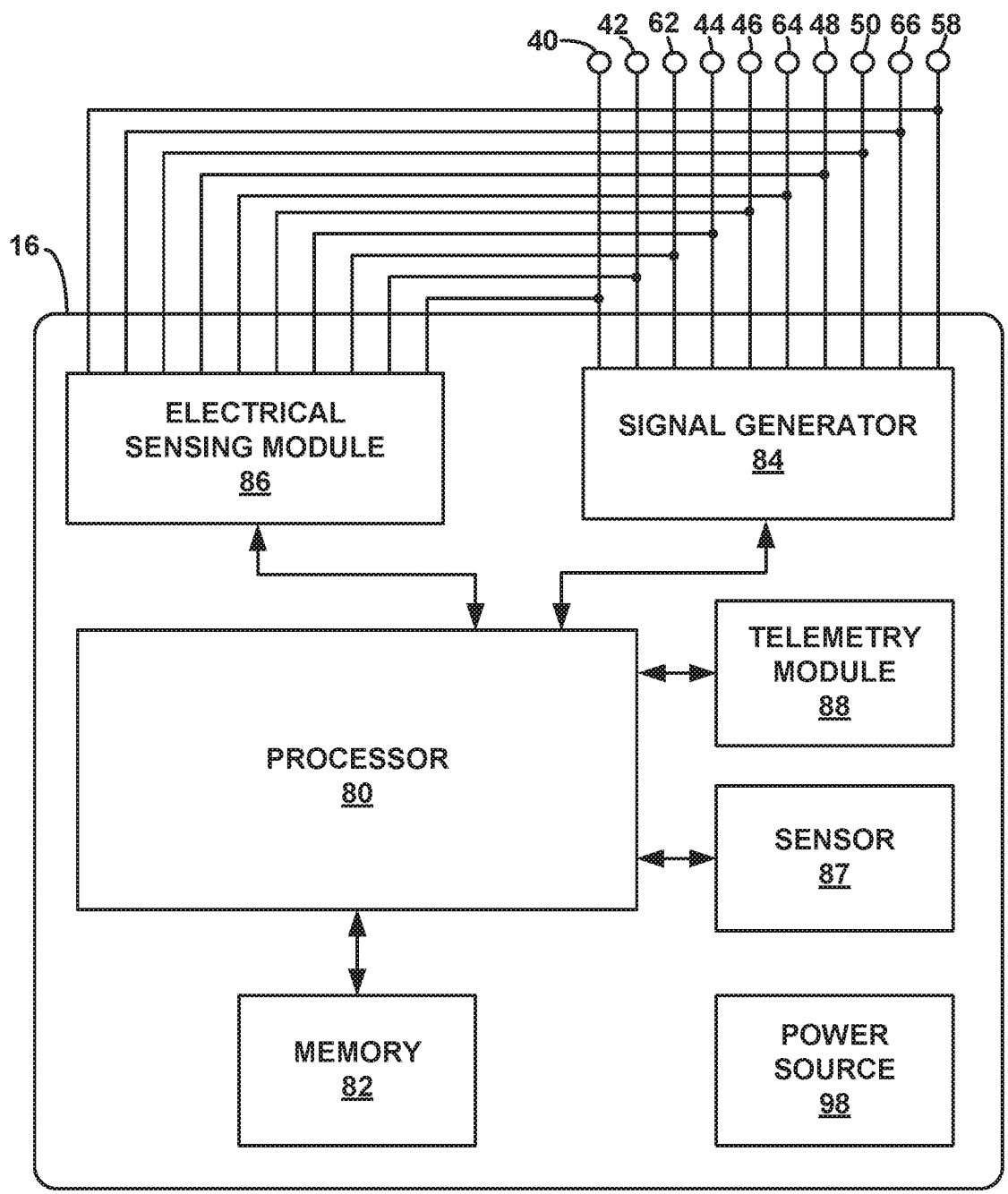
FIG. 4 is a functional block diagram illustrating an example configuration of an IMD.

FIG. 4 is a functional block diagram illustrating one example configuration of IMD 16 including processor 80, memory 82, signal generator 84, electrical sensing module 86, sensor 87, telemetry module 88, and power source 98. Memory 82 may include computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. Processor 80 controls signal generator 84 to deliver stimulation therapy to heart 12 according to operational parameters or programs, which may be stored in memory 82.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. Signal generator 84 may also deliver AV nodal stimulation via electrodes 48, 50, and/or 66 of RA lead 22, e.g., in a bipolar configuration or in a unipolar configuration in combination with housing electrode 58. In some examples, signal generator 84 delivers one or more of these types of stimulation in the form of electrical pulses. In other examples, signal generator 84 may deliver one or more of these types of stimulation in the form of other signals, such as sine waves, square waves, or other substantially continuous time signals.

In some examples, signal generator 84 is configured to deliver AV nodal stimulation in the form of a series of high frequency pulses. For example, signal generator 84 may deliver AV nodal stimulation, e.g., via electrodes 48, 50, and/or 66 of RA lead 22, in a burst pattern characterized by a plurality of pulse trains of high frequency pulses. This burst pattern may be particularly effective in interrupting the conduction of cardiac impulses across the AV node to reduce the ventricular rate response during an atrial tachyarrhythmia, e.g. atrial fibrillation.

In some examples, the effect of AV nodal stimulation delivered to patient 14 may take a period of time to subside after signal generator stops delivering the stimulation. As such, in one example, signal generator 84 may be configured to deliver AV nodal stimulation, stop delivering stimulation for a period of time, e.g. one or more depolarization/repolarization cycles of heart 12, and then begin delivering AV nodal stimulation again.

Memory 82 may store values for stimulation parameters that processor 80 accesses to control delivery of AV nodal stimulation by signal generator 84. Such stimulation parameters may include pulse duration, pulse train duration, the number of pulses in a pulse train, pulse amplitude, pulse frequency, and pulse train frequency. As one example, signal generator 82 may control stimulation using a pulse duration of approximately 0.2 milliseconds, a pulse train duration of approximately 250 milliseconds, an amplitude of approximately 4 volts, a pulse frequency of approximately 50 hertz, and a pulse train frequency of approximately 80 pulse trains per minute. These values merely are examples and other values are also contemplated.

In some examples, memory 82 may store other operation parameters of IMD 16 by which the device delivers stimulation to patient 12 including, e.g., threshold atrial tachyarrhythmia detection criteria, ventricular tachyarrhythmia event count, and stimulation termination criteria. For example, memory 82 may store values of parameters related to as well as instructions for detecting indications of sinus tachycardia as a threshold to detecting an atrial tachyarrhythmia. As another example, memory 82 store particular atrial and ventricular intervals or groups of intervals employed by processor 80 of IMD 16 to detect an atrial tachyarrhythmia. For example, memory 82 may store a median P-P interval and/or a median R-R interval for heart 12 of patient 14. In another example, memory 82 stores one or more termination criteria employed by IMD 16 to determine when to terminate delivering AV nodal stimulation to patient 14.

In some examples, memory 82 may also store suitable ranges for one or more stimulation parameters. As one example, memory 82 stores a pulse frequency range of approximately 20 Hz to approximately 100 Hz. In other examples, the pulse frequency may fall outside of this range.

In another example, memory 82 stores an amplitude range of approximately 0.5 volts to approximately 8 volts.

In one example, signal generator 84 may be configured to deliver stimulation adaptively to patient 14 according to parameters that are determined based on the effect of past stimulation. In one example, processor 80 may control stimulation generator 84 to deliver stimulation to patient 14 including one or more of frequency, pulse width, and amplitude values set based on a measured effect of past stimulation, or other physiological responses or parameters of the patient. Adaptive stimulation may save energy and extend the longevity of IMD 16.

Signal generator 84 may include a switch module and processor 80 may use the switch module to select, e.g., via a data/address bus, which of the available electrodes are used to deliver stimulation signals, e.g., defibrillation, pacing, and/or AV nodal stimulation signals. The switch module may include a switch array, switch matrix, multiplexer, or any other type of switching device suitable to selectively couple a signal to selected electrodes.

Electrical sensing module 86 monitors signals from at least one of electrodes 40, 42, 44, 46, 48, 50, 58, 62, 64 or 66 in order to monitor electrical activity of heart 12. Electrical sensing module 86 may also include a switch module to select which of the available electrodes are used to sense the heart activity. In some examples, processor 80 may select the electrodes that function as sense electrodes, or the sensing configuration, via the switch module within electrical sensing module 86, e.g., by providing signals via a data/address bus.

In some examples, electrical sensing module 86 includes multiple detection channels, each of which may comprise an amplifier. Each sensing channel may detect electrical activity in respective chamber of heart 12, and may be configured to detect either R-waves or P-waves. In some examples, electrical sensing module 86 or processor 80 may include an analog-to-digital converter for digitizing the signal received from a sensing channel for electrogram signal processing by processor 80. In response to the signals from processor 80, the switch module within electrical sensing module 86 may couple the outputs from the selected electrodes to one of the detection channels or the analog-to-digital converter.

During pacing, escape interval counters maintained by processor 80 may be reset upon sensing of R-waves and P-waves with respective detection channels of electrical sensing module 86. Signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one or more of the chambers of heart 12. Processor 80 may control signal generator 84 to deliver a pacing pulse to a chamber upon expiration of an escape interval. Processor 80 may reset the escape interval counters upon the generation of pacing pulses by stimulation generator 84, or detection of an intrinsic depolarization in a chamber, and thereby control the basic timing of cardiac pacing functions. The escape interval counters may include P-P, V-V, RV-LV, A-V, A-RV, or A-LV interval counters, as examples. The value of the count present in the escape interval counters when reset by sensed R-waves and P-waves may be used by processor 80 to measure the durations of R-R intervals, P-P intervals, P-R intervals and R-P intervals. Processor 80 may use the count in the interval counters to detect a tachyarrhythmia event, such as an atrial or ventricular fibrillation or tachycardia and/or detect a heart rate, such as an atrial rate or ventricular rate. For example, processor 80 may measure and record a number of P-P intervals and R-R intervals for heart 12, from which the processor may detect an atrial tachyarrhythmia by detecting a median P-P interval in heart 12 of patient 14 that is less than a percentage threshold of a median R-R interval of the heart.

Processor 80 may also derive other physiological parameters from signals sensed via electrical sensing module 86. For example, processor 80 may establish one or more indicators of ejection fraction and/or heart failure status from electrical signals sensed via electrical sensing module 86. In particular, impedance signals may be used to determine flow or pressure, which may indicate ejection fraction and/or heart failure status.

In one example, processor 80, in conjunction with memory 82, signal generator 84, and sensing module 86 detects an atrial tachyarrhythmia, such as atrial fibrillation, and delivers AV nodal stimulation to reduce the ventricular rate response to the atrial tachyarrhythmia. For example, processor 80 monitors heart 12 of patient 14 for a ventricular tachyarrhythmia by controlling sensing module 86 to configure one or more electrodes connected to one or more of leads 18, 20 and 22 as sense electrodes and by employing any of a number of appropriate ventricular tachyarrhythmia detection techniques.

In addition to monitoring heart 12 for a ventricular tachyarrhythmia, processor 80 may be configured to detect an atrial tachyarrhythmia by controlling sensing module 86 to employ, e.g., RA lead 22 positioned to sense electrical activity within right atrium 26. In one example, as a threshold to detecting an arrhythmia in heart 12 of patient 14, processor 80 of IMD 16 analyzes the rhythm of heart 12 for indications of sinus tachycardia. Accelerated heart rates, such as an atrial or ventricular tachyarrhythmia, commonly indicate conditions for which patient 14 may need therapy. However, rapid heart rates are also caused by normal physiological conditions including, e.g., exercise, stress, and certain emotional responses. Analyzing the rhythm of heart 12 of patient 14 for indications of sinus tachycardia, therefore, provides a confirmation that a treatable arrhythmia versus normal physiological response is occurring in the patient's heart.

In one example, processor 80 is programmed to control sensing module 86 to sense cardiac electrograms (EGMs) of heart 12, from which processor 80 determines if the R-R interval of heart 12 is approximately equal to the P-P interval. A one-to-one ratio between R-R and P-P intervals indicates balanced atrial and ventricular contraction rates, which may be indicative of a sinus tachycardia versus a tachyarrhythmia. In another example, processor 80 determines if R-R interval and/or the P-R interval are within a set physiological limit for patient 14, which may also be indicative of a sinus tachycardia versus a tachyarrhythmia.

In addition to checking for indications of sinus tachycardia, processor 80 may also control sensing module 86 to monitor EGMs from heart 12 to measure one or more P-P and R-R intervals. In some examples, atrial tachyarrhythmia is indicated by more contractions in atria 26, 36 than in ventricles 28, 32 of heart 12. P-P interval is a measure of the length of the depolarization and repolarization cycle of atria 26, 36. Similarly, R-R interval is a measure of the length of the depolarization and repolarization cycle of ventricles 28, 32. As such, the contraction rate of atria 26, 36 increases, as the P-P interval decreases. Processor 80 may therefore employ sensing module 86 to detect an atrial tachyarrhythmia by, e.g., detecting a P-P interval in heart 12 of patient 14 that is less than a percentage threshold of an R-R interval of the heart. In some examples, processor 80 controls sensing module 86 to monitor heart 12 and stores a number of P-P and R-R intervals on memory 82. Processor 80 calculates a median P-P and R-R interval from the stored values on memory 82. Processor 80 then compares a median P-P interval to a median R-R interval. The percentage threshold of the R-R interval may be based on empirical data indicating at what differential between the number of atrial and ventricular contractions is an atrial tachyarrhythmia indicated. In one example, processor 80 detects an atrial tachyarrhythmia when the device detects a median P-P interval that is less than approximately 93.75% of a median R-R interval.

In order to mitigate the risk of misdiagnosis and inappropriate therapy delivery based thereon, processor 80 of IMD 16 may be programmed to anticipate imminent ventricular tachyarrhythmia detection and take measures prior to such detection. In one example, processor 80 controls sensing module 86 to monitor heart 12 for ventricular tachyarrhythmia events, e.g., intervals between consecutive ventricular depolarizations that are less than a tachyarrhthmia threshold. Processor 80 increments a counter stored on memory 82 upon detection of each such event by sensing module 86. Processor 80 may anticipate a ventricular tachyarrhythmia detection when the ventricular tachyarrhythmia event count stored in memory 82 exceeds a threshold value, also stored, e.g., in memory 82. By anticipating a potentially incorrect ventricular tachyarrhythmia detection, processor 80 is able to intervene with AV nodal stimulation to reveal rapid ventricular conduction during atrial tachyarrhthmia masked as ventricular tachyarrhythmia before the device incorrectly diagnoses and treats patient 14. Conversely, processor 80 need not intervene with stimulation until an imminent detection is indicated with a threshold confidence by basing the anticipation of a ventricular tachyarrhythmia on a number of events indicative of such a condition.

IMD 16 may take one more precautions as a precondition to delivering AV nodal stimulation to heart 12 to reduce the ventricular rate response to an atrial tachyarrhythmia. In some examples, processor 80 of IMD 16 may control sensing module 86 to measure the R-R interval of heart 12 to confirm that the contraction rate of ventricles 28, 32 is in a range appropriate for intervening with AV nodal stimulation. In particular, processor 80 may control sensing module 86 to measure a number of R-R intervals of heart 12, from which processor 80 determines a median R-R interval to confirm that the contraction rate of ventricles 28, 32 is below a maximum threshold and above a minimum threshold. For example, a supraventricular tachycardia for which AV nodal stimulation may be employed is not likely if the ventricular contraction rate is too fast (i.e. RR median is too low), e.g. if the rate is greater than 240 beats per minute (bpm). Conversely, if the contraction rate of ventricles 28, 32 is too slow (i.e. R-R median too high), the ventricular conduction through the AV node during atrial tachyarrhythmia is likely not rapid enough to even warrant attention, let alone intervention with stimulation. Therefore, processor 80 may not control signal generator 84 to deliver AV nodal stimulation, unless the median R-R interval is below the maximum threshold and above the minimum threshold.

In some examples, in the event an atrial tachyarrhythmia is detected, and a ventricular tachyarrhythmia is not detected but a ventricular tachyarrhythmia detection is anticipated, processor 80 may control signal generator 84 to deliver AV nodal stimulation to patient 14. In one example, processor 80 controls signal generator 84 to employ one or more electrodes of RA lead 22 to deliver stimulation to or proximate to the AV node, e.g., to or proximate to the AV nodal fat pad. Signal generator 84 may deliver such stimulation in the form of bursts of pulses or a continuous train of pulses. The stimulation may be delivered by signal generator 84 according to one or more programmed stimulation parameters stored in memory 82 including, e.g., amplitude, pulse width and frequency, as well as the number of pulses within a burst. For example, signal generator 84 may deliver AV nodal stimulation via electrodes on lead 22 with a frequency in a range from approximately 20 Hz to approximately 100 Hz, and amplitude in a range from approximately 0.5 volts to approximately 8 volts. Processor 80 controls signal generator to deliver electrical stimulation to patient 14 to block the AV node of heart 12, which may act to reduce ventricular conduction and contraction rate caused by a supraventricular tachycardia, e.g., during an atrial fibrillation.

IMD 16 may, in some examples, also be programmed with stimulation parameters configured to act as safety precautions to guard against vagal stimulation preventing appropriate sensing in ventricles 28, 32. As signal generator 84 delivers high frequency stimulation, e.g., in the form of bursts of pulses, blanking periods in which the device does not sense ventricular activity accumulate. There is a risk, as IMD 16 delivers high frequency stimulation, that the blanking periods, and therefore the stimulation burst time periods reach a threshold level beyond which IMD 16 may not be able to detect the development of serious arrhythmias in ventricles 28, 32, e.g. ventricular fibrillation. The stimulation frequency may therefore be bounded by limits that are designed to prevent the accumulation of blanking periods beyond a threshold level. For example, a period of time over which a stimulation burst is delivered by signal generator 84 may be based on the contraction frequency in ventricles 28, 32 such that the burst period does not subsume the period between ventricular contractions. In this manner, processor 80 of IMD 16 may base the stimulation burst period over which a burst of stimulation is delivered by signal generator 84 on, e.g., a median R-R interval for heart 12. In one example, processor 80 may control signal generator 84 to deliver a stimulation burst for a period of time based on, e.g., a median R-R interval for heart 12 as calculated by processor 80 from a number of R-R intervals measured by sensing module 86. In one example, processor 80 may limit the stimulation burst period to approximately 50% of a median R-R interval for heart 12 of patient 14 such that 50% of the time between ventricular contractions the stimulation burst is delivered and 50% of the time is retained for sensing the activity of ventricles 28, 32.

In other examples, IMD 16 may also be configured to synchronize the delivery of AV nodal stimulation with a QRS complex of heart 12. In particular, IMD 16 may be configured to deliver, e.g. AV nodal vagal stimulation in a refractory period between depolarization/repolarization cycles. During the refractory period, the stimulation is less likely to depolarize heart 12, and, in particular, ventricles 28, 32.

IMD 16 continues to deliver AV nodal stimulation until one or more stimulation termination criteria are satisfied, at which point the device terminates the stimulation. In one example, the termination criteria includes at least one of expiration of a programmed AV nodal stimulation delivery time period, an accumulation of blanking time periods that exceeds a threshold percentage of a AV nodal stimulation delivery time period, failure to detect a threshold ventricular rate response within a AV nodal stimulation response time period, or detection of a ventricular tachyarrhythmia.

In some examples, IMD 16 is programmed, e.g. according to a therapy program stored in memory 82 to deliver AV nodal stimulation for a specific period of time. The programmed stimulation time period may be set to a value that provides a sufficient amount of time for IMD 16 to test the effectiveness of the stimulation in modulating the ventricular rate response. Additionally, regardless of other termination criteria, the stimulation time period may be set to a value that provides hysteresis such that IMD 16 is not rapidly toggling between turning AV nodal stimulation on and off. In one example, processor 80 of IMD 16 is programmed with a AV nodal stimulation time period stored in memory 82 in a range from approximately 20 seconds to approximately 30 seconds.

As described above with reference to the parameters by which IMD 16 delivers AV nodal stimulation to patient 14, there is a risk that, as IMD 16 delivers high frequency stimulation bursts, blanking periods will accumulate beyond a threshold such that sensing module 86 may not be able to detect the development of a ventricular tachyarrhythmia, e.g. ventricular fibrillation in heart 12 of patient 14. Processor 80 may, therefore, be programmed to control sensing module 86 to monitor the AV nodal stimulation delivered by signal generator 84 and the periods of time sensing module 86 is sensing activity in ventricles 28, 32 during stimulation to ensure that an accumulated blanking period, i.e. an accumulation of stimulation burst periods does not exceed a threshold percentage of the total time over which AV nodal stimulation is delivered. In one example, the threshold percentage is 50% such that, for example, during 30 seconds of AV nodal stimulation a window of at least 15 seconds in which sensing module 86 may sense activity in ventricles 28, 32 is needed. In the event the 50% threshold is exceeded by the accumulated blanking period, e.g. sensing module 86 only senses activity in heart 12 for 10 seconds of a 30 second period, processor 80 may control signal generator 84 to terminate delivery of AV nodal stimulation to patient 14.

In another example, processor 80 controls sensing module 86 and signal generator 84 based on each stimulation burst or series of stimulation pulses such that the stimulation burst period does not exceed a threshold percentage of the period between ventricular depolarizations. In one example, processor 80 may limit the stimulation burst period delivered by signal generator 84 to approximately 50% of a median R-R interval for heart 12 of patient 14 such that 50% of the time between ventricular contractions the stimulation burst is delivered and 50% of the time is retained for sensing the activity of ventricles 28, 32.

As explained above with reference to FIG. 1, in some examples, processor 80 may be programmed to allow the stimulation burst period to exceed a threshold percentage of the depolarization frequency in ventricles 28, 32 for a brief period at the beginning of the delivery of AV nodal stimulation before the effect of the stimulation is able to slow the depolarizations of ventricles 28, 32.

In addition to stimulation time period expiration and blanking period accumulation, processor 80 may be programmed to control signal generator 84 to terminate the delivery of AV nodal stimulation in the event a minimum ventricular rate response is not observed within a programmed response time period. In one example, processor 80 may be programmed to terminate AV nodal stimulation if the contraction rate of ventricles 28, 32 does not decrease by a threshold amount within the stimulation response time period. The minimum ventricular rate response may differ from one patient to another and may be set as a relative percentage reduction or as an absolute value rate reduction. In examples in which the minimum rate response is set as an absolute value, the value by which processor 80 measures rate response may be tiered depending on the observed contraction rate of ventricles 28, 32, e.g. the minimum rate response may be higher for higher initial ventricular contraction rates and lower for lower ventricular contraction rates.

In one example, processor 80 is programmed with a AV nodal stimulation response time period of approximately 10 seconds or in a range of 5 to 10 beats of heart 12. Additionally, processor 80 is programmed with a minimum rate response approximately equal to a 20% rate reduction from the initial contraction rate of ventricles 28, 32 measured by sensing module 86. In another example, IMD 16 is programmed with a minimum rate response approximately equal to 40 bpm for higher initial ventricular contraction rates on the order of 180 bpm or higher, and a minimum rate response approximately equal to 20 bpm for lower initial ventricular contraction rates on the order of 120 bpm or lower. The stimulation response time period and minimum ventricular rate response values, which are employed by processor 80 as basis for controlling signal generator 84 to terminate stimulation, may, in some examples, be stored in memory 82 of IMD 16.

IMD 16 may also include one or more sensors 87 separate from electrodes 40, 42, 44, 46, 48, 50, 58, 62, 64 and 66. Via a signal generated by sensor 87, processor may monitor one or more physiological parameters indicative of cardiac contraction, autonomic tone, heart failure, and/or ejection fraction. Examples of sensors 87 that may generate a signal indicative of cardiac contraction include a intracardiac or intravascular pressure sensor, an accelerometer or other sensor capable of detecting heart or blood sounds, vibrations, or motion, an optical or ultrasonic sensor capable of detecting changes in flow associated with cardiac contractions, or an optical sensor capable of detecting oxygen saturation changes associated with cardiac contractions. Processor 80 may detect cardiac contractions based on signals from one or more sensors 87, and detect arrhythmias based on the detected cardiac contractions.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and receive downlinked data from programmer 24 via an address/data bus. In some examples, telemetry module 88 may provide received data to processor 80 via a multiplexer.

In some examples, processor 80 transmits indications of detected atrial tachyarrhythmias and the ventricular rate response therefrom via telemetry module 88. Processor 80 may also transmit, via telemetry module 88, information regarding AV nodal stimulation delivered by signal generator 84 and a response to AV nodal stimulation, e.g., detected by electrical sensing module 86.

The various components of IMD 16 are coupled to power source 90, which may include a rechargeable or non-rechargeable battery. A non-rechargeable battery may be capable of holding a charge for several years, while a rechargeable battery may be inductively charged from an external device, e.g., on a daily or weekly basis. In other examples, power source 90 may include a supercapacitor.

Figure 5:
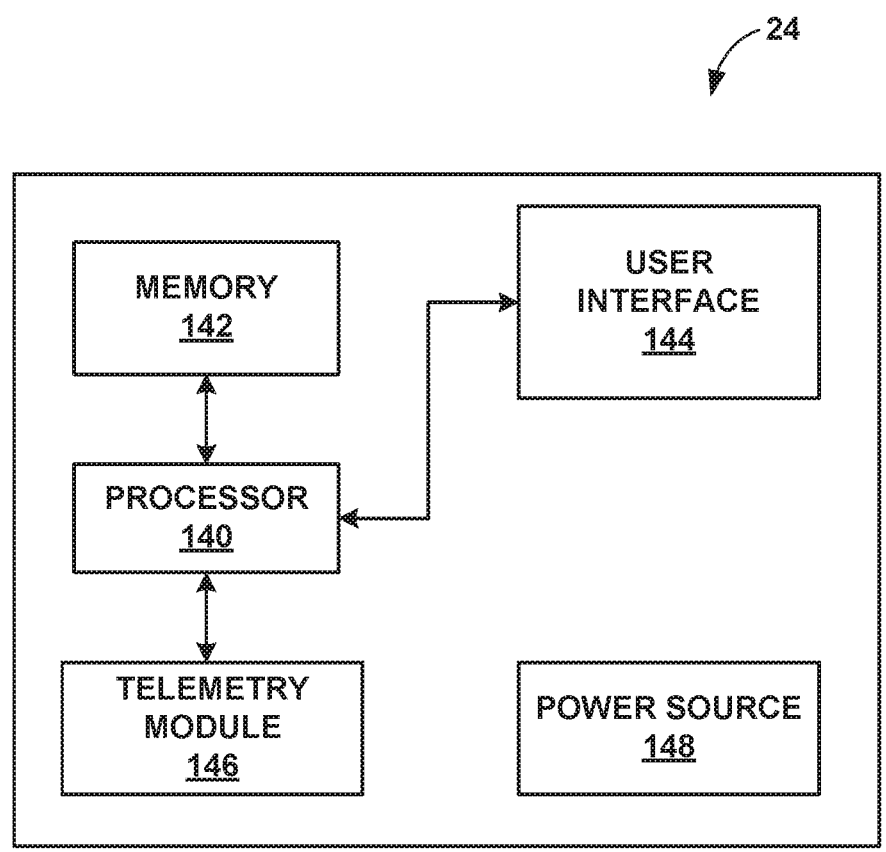
FIG. 5 is block diagram of an example external programmer that facilitates user communication with the IMD.

FIG. 5 is block diagram of an example configuration of programmer 24. As shown in FIG. 5, programmer 24 includes processor 140, memory 142, user interface 144, telemetry module 146, and power source 148. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of operational parameters), generate new therapy programs, or modify therapy programs for IMD 16. The clinician may interact with programmer 24 via user interface 144 which may include a display to present a graphical user interface to a user, and a keypad or another mechanism for receiving input from a user.

Processor 140 can take the form one or more microprocessors, DSPs, ASICs, FPGAs, programmable logic circuitry, or the like, and the functions attributed to processor 102 herein may be embodied as hardware, firmware, software or any combination thereof. Memory 142 may store instructions that cause processor 140 to provide the functionality ascribed to programmer 24 herein, and information used by processor 140 to provide the functionality ascribed to programmer 24 herein. Memory 142 may include any fixed or removable magnetic, optical, or electrical media, such as RAM, ROM, CD-ROM, hard or floppy magnetic disks, EEPROM, or the like. Memory 142 may also include a removable memory portion that may be used to provide memory updates or increases in memory capacities. A removable memory may also allow patient data to be easily transferred to another computing device, or to be removed before programmer 24 is used to program therapy for another patient. Memory 142 may also store information that controls therapy delivery by IMD 16, such as stimulation parameter values associated with AV nodal vagal stimulation delivered by signal generator 84 of IMD 16.

Programmer 24 may communicate wirelessly with IMD 16, such as using RF communication or proximal inductive interaction. This wireless communication is possible through the use of telemetry module 146, which may be coupled to an internal antenna or an external antenna. An external antenna that is coupled to programmer 24 may correspond to the programming head that may be placed over heart 12, as described above with reference to FIG. 1. Telemetry module 146 may be similar to telemetry module 88 of IMD 16 (FIG. 3).

Telemetry module 146 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 140 may be configured to provide some or all of the functionality ascribed to processor 80 of IMD 16 herein. For example, processor 140 may receive indications of cardiac depolarizations or contractions, a signal from one or more sensors 87, or information regarding detected atrial tachyarrhythmias and the ventricular rate response to the detected arrhythmias from IMD 16 via telemetry module 146. In some examples, processor 140 may initiate or modify AV nodal stimulation by controlling signal generator 84 and sensing module 86 via telemetry modules 146, 88, as described herein with respect to IMD 16 and processor 80.

Figure 6:
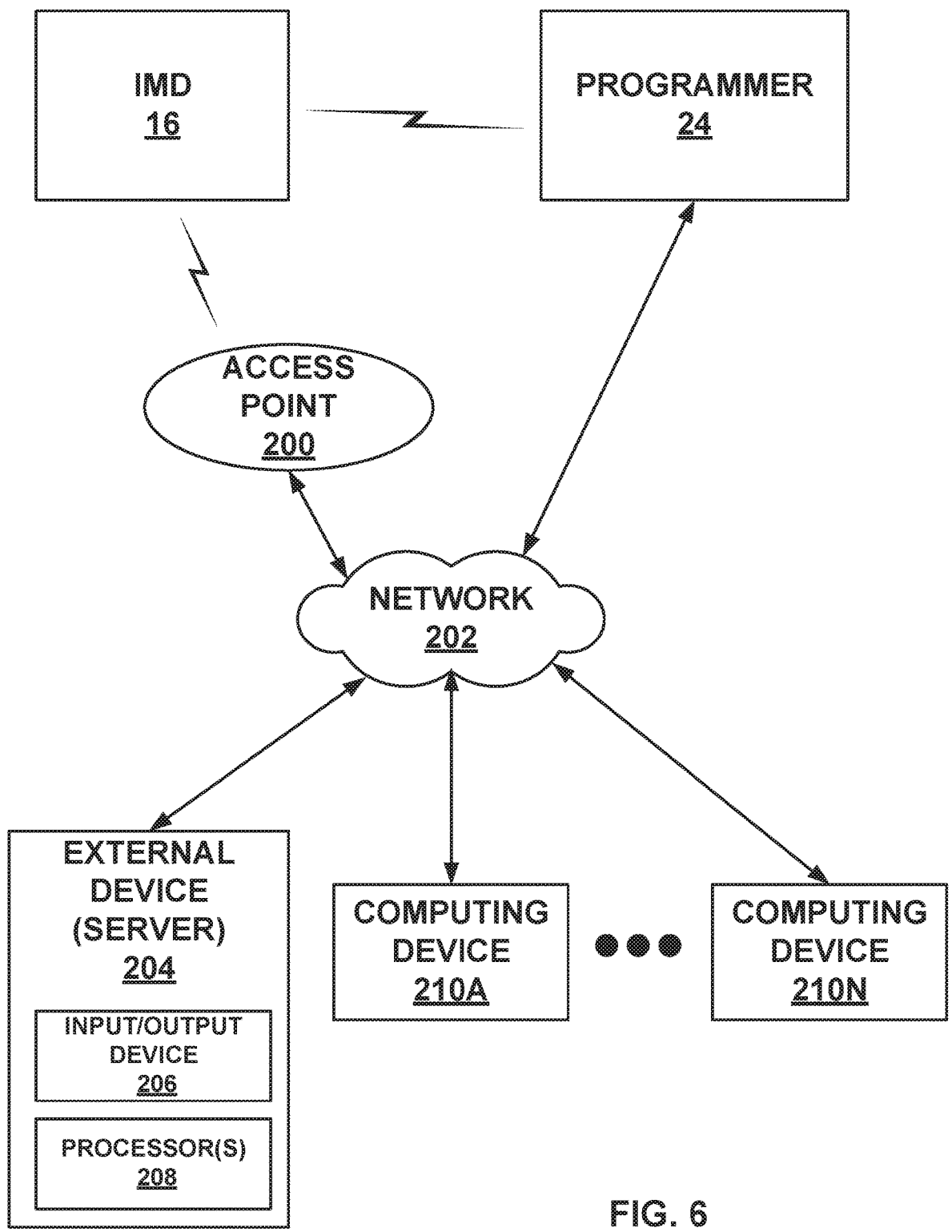
FIG. 6 is a block diagram illustrating an example system that includes an external device, such as a server, and one or more computing devices that are coupled to the IMD and programmer shown in FIG. 1 via a network.

FIG. 6 is a block diagram illustrating an example system that includes an external device, such as a server 204, and one or more computing devices 210A-210N, that are coupled to the IMD 16 and programmer 24 shown in FIG. 1 via a network 202. In this example, IMD 16 may use its telemetry module 88 to communicate with programmer 24 via a first wireless connection, and to communication with an access point 200 via a second wireless connection. In the example of FIG. 6, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described above with reference to processor 80 of IMD 16 and processor 140 of programmer 24.

Access point 200 may comprise a device that connects to network 202 via any of a variety of connections, such as telephone dial-up, digital subscriber line (DSL), or cable modem connections. In other examples, access point 200 may be coupled to network 202 through different forms of connections, including wired or wireless connections. In some examples, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16.

In some cases, server 204 may be configured to provide a secure storage site for data that has been collected from IMD 16 and/or programmer 24. Network 202 may comprise a local area network, wide area network, or global network, such as the Internet. In some cases, programmer 24 or server 206 may assemble data in web pages or other documents for viewing by trained professionals, such as clinicians, via viewing terminals associated with computing devices 210A-210N. The illustrated system of FIG. 6 may be implemented, in some aspects, with general network technology and functionality similar to that provided by the Medtronic CareLink® Network developed by Medtronic, Inc., of Minneapolis, MN.

In some examples, processor 208 of server 204 may be configured to provide some or all of the functionality ascribed to processor 80 of IMD 16 herein. For example, processor 206 may receive indications of cardiac depolarizations or contractions, a signal from one or more sensors 87, or information regarding detected atrial tachyarrhythmias and the ventricular rate response to the detected arrhythmias from IMD 16 via access point 200 or programmer 24 and network 202. Processor 206 may also initiate and/or terminate AV nodal stimulation delivered by signal generator 84 of IMD 16. In some examples, server 204 relays received indications of cardiac depolarizations or contractions, a signal from one or more sensors 87, or information regarding detected atrial tachyarrhythmias and the ventricular rate response thereto provided by one or more of IMD 16 or programmer 24 to one or more of computing devices 210 via network 202. A processor of a computing device 210 may similarly provide some or all of the functionality ascribed to processor 80 of IMD 16 herein.

Figure 7:
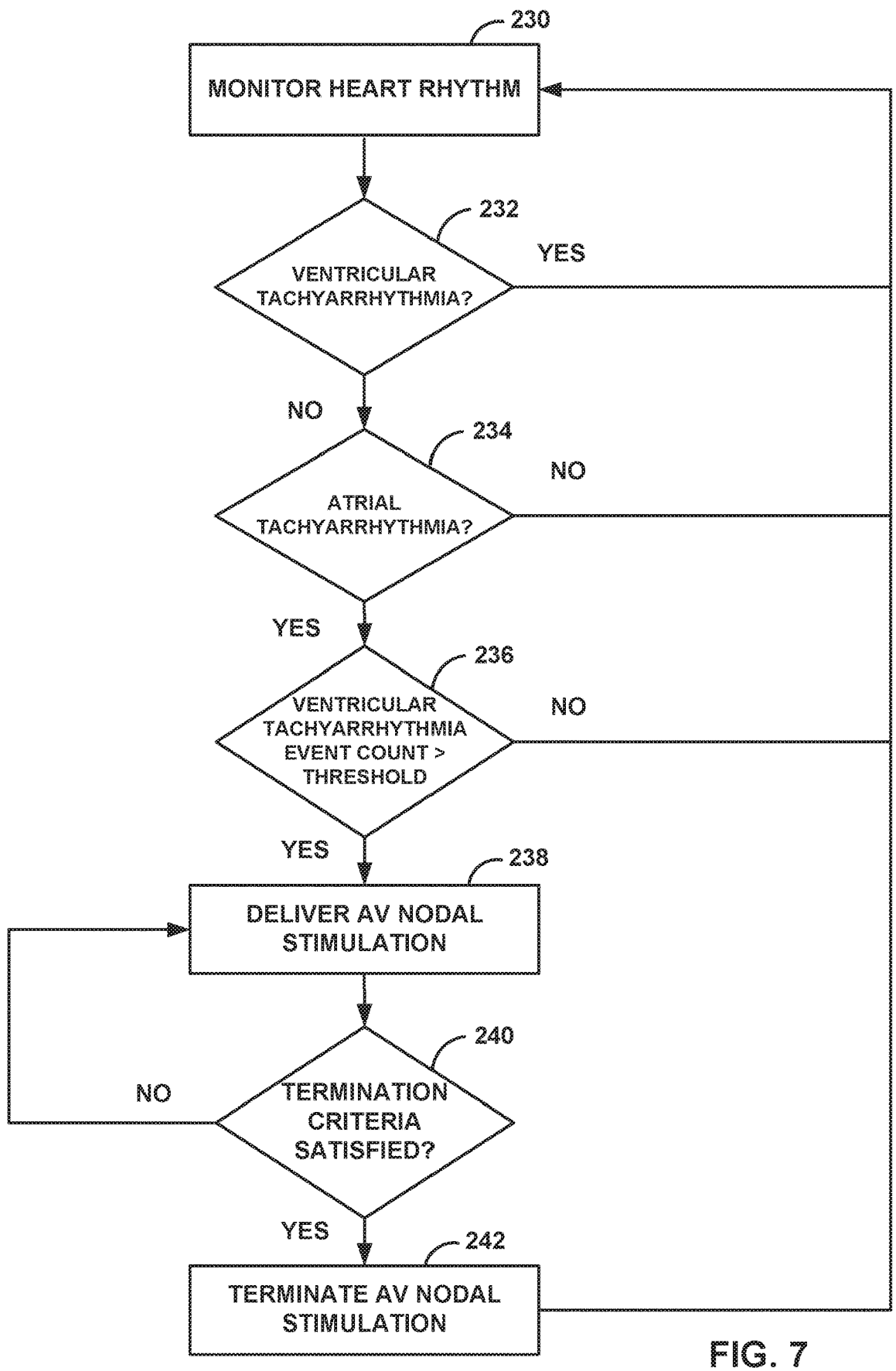
FIG. 7 is a flow diagram of an example method of delivering vagal stimulation to a patient.

FIG. 7 is a flow diagram of an example method of delivering AV nodal stimulation to patient 14. The method of FIG. 7 includes monitoring a rhythm of a heart of a patient (230), determining if a ventricular tachyarrhythmia is occurring in the patient's heart (232), detecting an atrial tachyarrhythmia (234), anticipating a ventricular tachyarrhythmia detection based on a threshold value of a ventricular tachyarrhythmia event count (236), delivering AV nodal stimulation to block the atrioventricular node of the heart of the patient (238), determining if one or more termination criteria have been satisfied (240), and terminating the delivery of AV nodal stimulation based on the stimulation termination criteria.

In one example, processor 80, in conjunction with memory 82, signal generator 84, and sensing module 86 detects an atrial tachyarrhythmia, such as atrial fibrillation, and delivers AV nodal vagal stimulation to reduce the ventricular rate response to the atrial tachyarrhythmia. For example, according to the method of FIG. 7, processor 80 monitors heart 12 of patient 14 (230) to determine if a ventricular tachyarrhythmia is occurring (232) by controlling sensing module 86 to configure one or more electrodes connected to one or more of leads 18, 20 and 22 as sense electrodes and by employing any of a number of appropriate ventricular tachyarrhythmia detection techniques.

In addition to monitoring heart 12 for a ventricular tachyarrhythmia (230, 232), processor 80 may be configured to detect an atrial tachyarrhythmia (234) by controlling sensing module 86 to employ, e.g., RA lead 22 positioned to sense electrical activity within right atrium 26. In one example, as a threshold to detecting an arrhythmia in heart 12 of patient 14 (234), processor 80 of IMD 16 analyzes the rhythm of heart 12 for indications of sinus tachycardia. Accelerated heart rates commonly indicate conditions for which patient 14 may need therapy, such as an atrial or ventricular tachyarrhythmia. However, rapid heart rates are also caused by normal physiological conditions including, e.g., exercise, stress, and certain emotional responses. Analyzing the rhythm of heart 12 of patient 14 for indications of sinus tachycardia, therefore, provides a confirmation that a treatable arrhythmia versus normal physiological response is occurring in the patient's heart.

In one example, processor 80 is programmed to control sensing module 86 to sense cardiac EGMs of heart 12, from which processor 80 determines if the R-R interval of heart 12 is approximately equal to the P-P interval. A one-to-one ratio between R-R and P-P intervals indicates balanced atrial and ventricular contraction rates, which may be indicative of a sinus tachycardia versus a tachyarrhythmia. In another example, processor 80 determines if R-R interval and/or the P-R interval are within a set physiological limit for patient 14, which may also be indicative of a sinus tachycardia versus a tachyarrhythmia.

In addition to checking for indications of sinus tachycardia, processor 80 may also control sensing module 86 to monitor the ECG of heart 12 to measure one or more P-P and R-R intervals in order to detect an atrial tachyarrhythmia in the heart of patient 14 (234). In some examples, atrial tachyarrhythmia is indicated by more contractions in atria 26, 36 than in ventricles 28, 32 of heart 12. P-P interval is a measure of the length of the depolarization and repolarization cycle of atria 26, 36. Similarly, R-R interval is a measure of the length of the depolarization and repolarization cycle of ventricles 28, 32. As such, the contraction rate of atria 26, 36 increases, as the P-P interval decreases. Processor 80 may therefore employ sensing module 86 to detect an atrial tachyarrhythmia (234) by, e.g., detecting a P-P interval in heart 12 of patient 14 that is less than a percentage threshold of an R-R interval of the heart. In some examples, processor 80 controls sensing module 86 to monitor heart 12 and stores a number of P-P and R-R intervals on memory 82. Processor 80 calculates a median P-P and R-R interval from the stored values on memory 82. Processor 80 then compares a median P-P interval to a median R-R interval. The percentage threshold of the R-R interval may be based on empirical data indicating at what differential between the number of atrial and ventricular contractions is an atrial tachyarrhythmia indicated. In one example, processor 80 detects an atrial tachyarrhythmia (234) when sensing module 86 detects a median P-P interval that is less than approximately 93.75% of a median R-R interval.

In some cases, atrial tachyarrhythmia may be preceded by a disbalance in the autonomic system of patient 14. The disbalance in the autonomic system of patient 14 may be detected by processor 80 controlling sensing module 86 to monitor the ECG of heart 12 to analyzing the frequency spectrum of the rhythm of the heart, heart rate turbulence, or t-wave alternans. By detecting autonomic disbalance, in some examples, IMD 16 may be able to detect an early warning signal of atrial tachyarrhythmia in patient 14 and begin delivering AV nodal stimulation before the onset of the tachyarrhythmia episode.

In order to mitigate the risk of misdiagnosis and inappropriate therapy delivery based thereon, processor 80 of IMD 16 may be programmed to anticipate imminent ventricular tachyarrhythmia detection (236) and take measures prior to such detection. In one example, processor 80 controls sensing module 86 to monitor heart 12 for ventricular tachyarrhythmia events, e.g. a threshold ventricular contraction rate. Processor 80 increments a counter stored on memory 82 upon detection of each such event by sensing module 86. Processor 80 may anticipate a ventricular tachyarrhythmia detection (236) when the ventricular tachyarrhythmia event count stored in memory 82 exceeds a threshold value, also stored, e.g., in memory 82. By anticipating a potentially incorrect ventricular tachyarrhythmia detection, processor 80 is able to intervene with vagal stimulation to reveal rapid ventricular conduction during atrial tachyarrhythmia masked as ventricular tachyarrhythmia before the device incorrectly diagnoses and treats patient 14. Conversely, processor 80 need not intervene with vagal stimulation until an imminent detection is indicated with a threshold confidence by basing the anticipation of a ventricular tachyarrhythmia on a number of events indicative of such a condition.

In some examples, IMD 16 may take certain precautions as a precondition to delivering AV nodal vagal stimulation to heart 12 (238) to reduce the ventricular rate response to an atrial tachyarrhythmia. In one example, processor 80 of IMD 16 controls sensing module 86 to measure the R-R interval of heart 12 to confirm that the depolarization rate of ventricles 28, 32 is in a range appropriate for intervening with vagal stimulation. In particular, processor 80 controls sensing module 86 to measure a number of R-R intervals of heart 12, from which processor 80 determines a median R-R interval to confirm that the depolarization rate of ventricles 28, 32 is below a maximum threshold and above a minimum threshold. For example, a supraventricular tachycardia for which AV nodal vagal stimulation may be employed is not likely if the ventricular contraction rate is too low (i.e. RR median is too low), e.g. if the rate is less than 240 bpm. Conversely, if the depolarization rate of ventricles 28, 32 is too slow (i.e. R-R median too high), the ventricular conduction through the AV node during atrial tachyarrhythmia is likely not rapid enough to warrant attention, let alone intervention with vagal stimulation. Therefore, processor 80 may not control signal generator 84 to deliver vagal stimulation, unless the median R-R interval is below the maximum threshold and above the minimum threshold.

In some examples, in the event a ventricular tachyarrhythmia is not detected (232), an atrial tachyarrhythmia is detected (234), and an imminent ventricular tachyarrhythmia detection is anticipated (236), processor 80 may control signal generator 84 to deliver vagal stimulation to patient 14 (238). In one example, processor 80 controls signal generator 84 to employ one or more electrodes of RA lead 22 to deliver stimulation to or proximate to the AV node, e.g., to or proximate to the AV nodal vagal fat pad. Signal generator 84 delivers vagal stimulation in the form of bursts of pulses or a continuous train of pulses. The stimulation may be delivered by signal generator 84 according to one or more programmed stimulation parameters stored in memory 82 including, e.g., amplitude, pulse width and frequency, as well as the number of pulses within a burst. For example, signal generator 84 may deliver vagal stimulation via electrodes on lead 22 with a frequency in a range from approximately 20 Hz to approximately 100 Hz, and amplitude in a range from approximately 0.5 volts to approximately 8 volts. Processor 80 controls signal generator 84 to deliver vagal stimulation to patient 14 (238) to block the AV node of heart 12, which may act to reduce ventricular conduction and contraction rate caused by a supraventricular tachycardia, e.g., during an atrial fibrillation.

Figure 8:
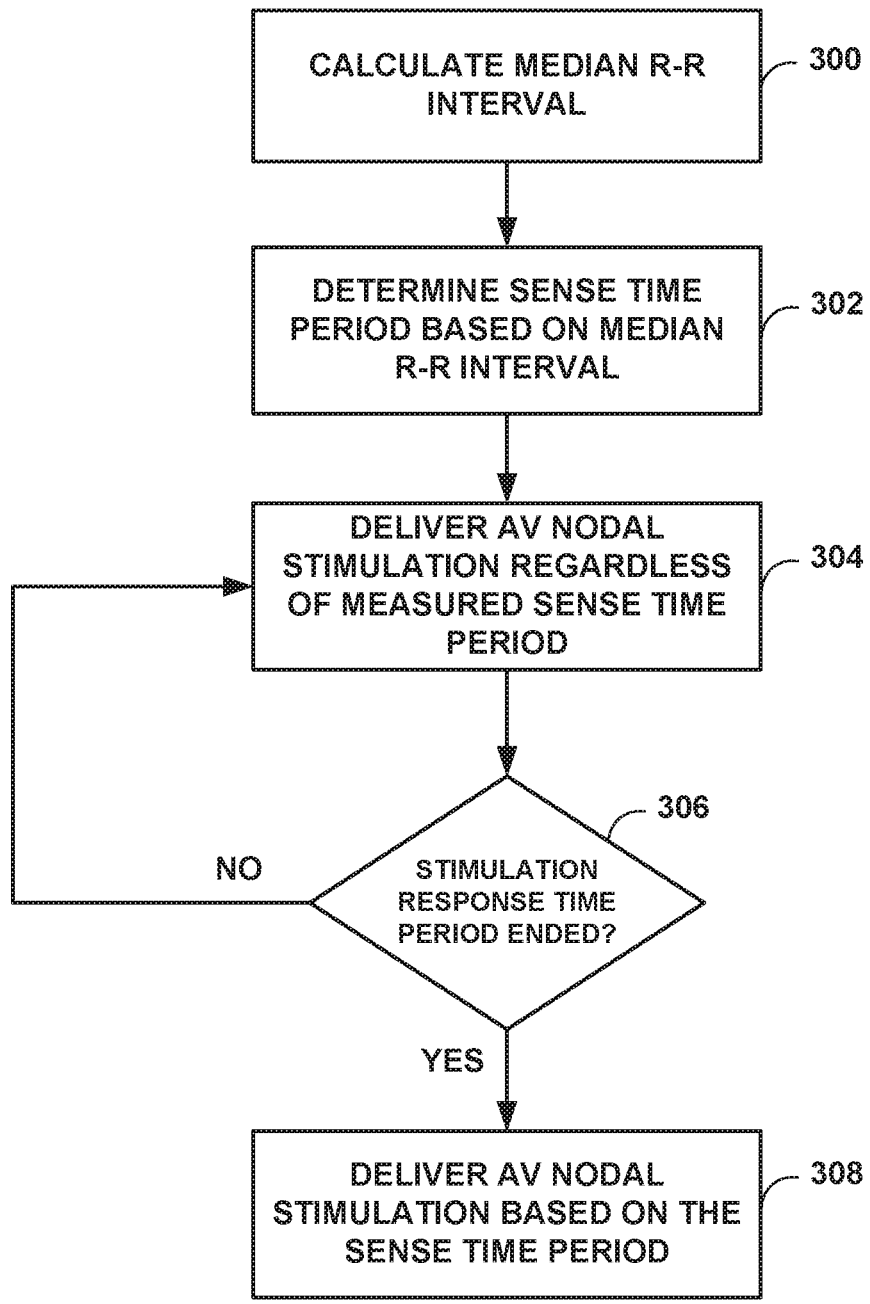
FIG. 8 is a flow diagram of one example of details of the method of delivering vagal stimulation to a patient illustrated in FIG. 7.

IMD 16 may, in some examples, also be programmed with stimulation parameters configured to act as safety precautions to guard against vagal stimulation preventing appropriate sensing in ventricles 28, 32. As signal generator 84 delivers high frequency stimulation, e.g., in the form of bursts of pulses to heart 12, blanking periods in which the device does not sense ventricular activity accumulate. There is a risk that the blanking periods will accumulate beyond a threshold such that sensing module 86 may not be able to detect the development of a ventricular tachyarrhythmia, e.g. ventricular fibrillation in heart 12 of patient 14. As such, in one example, delivering AV nodal, e.g. vagal stimulation to patient 14 (238) may include determining an amount of time over which ventricular depolarizations need to be sensed during the delivery of stimulation and delivering the stimulation based on the determined amount of time. FIG. 8 is a flowchart illustrating one example in which delivering AV nodal stimulation to patient 14 (238) includes determining an amount of time over which ventricular depolarizations need to be sensed during the delivery of stimulation and delivering the stimulation based on the determined amount of time.

In FIG. 8, delivering AV nodal stimulation to patient 14 (238) includes calculating a median R-R interval (300), determining a sense time period based on the median R-R interval (302), delivering AV nodal stimulation (304), determining if a stimulation response time has ended (306) and, if the response time has not ended, continuing to deliver AV nodal stimulation (304). If, however, the stimulation response time has ended, AV nodal stimulation is thereafter delivered based on the sense time period (308).

In one example of delivering AV nodal stimulation to patient 14 (238) according to the method of FIG. 8, processor 80 of IMD 16 may be configured to monitor heart 12 over a period of time and store a number of R-R intervals measured by sensing module 86 in memory 82. Based on the measured R-R intervals, processor 80 may calculate a median R-R interval (300).

Processor 80 may determine a sense time period over which ventricular depolarizations need to be sensed during the delivery of, e.g. AV nodal vagal stimulation by signal generator 84 based on the median R-R interval (302). In one example, processor 80 determines that the sense time period needs to be a threshold percentage of the median R-R interval such that accumulated stimulation burst periods and associated blanking periods do not subsume the period between ventricular contractions. In one example, processor 80 determines that the sense time period needs to be approximately 50% of the median R-R interval.

The method of delivering AV nodal stimulation to patient 14 (238) illustrated in FIG. 8 also includes, delivering AV nodal stimulation regardless of a measured sense time period (304) and determining, after initiating the stimulation, if a stimulation response period has ended (306). The stimulation response period is a period over which a minimum ventricular rate response is expected and may be expressed, e.g. in terms of a time or an absolute or relative response in the measured ventricular rate. As noted above, IMD 16 may be configured to allow the accumulation of blanking periods for a brief period of time upon initially delivering vagal stimulation to patient 14. As such, in one example, processor 80 controls signal generator 84 to deliver AV nodal stimulation for a brief period of time, in the example of FIG. 8 until the response time period ends, regardless of the actual sense time period measured by the processor based on information from sensing module 86.

Figure 9:
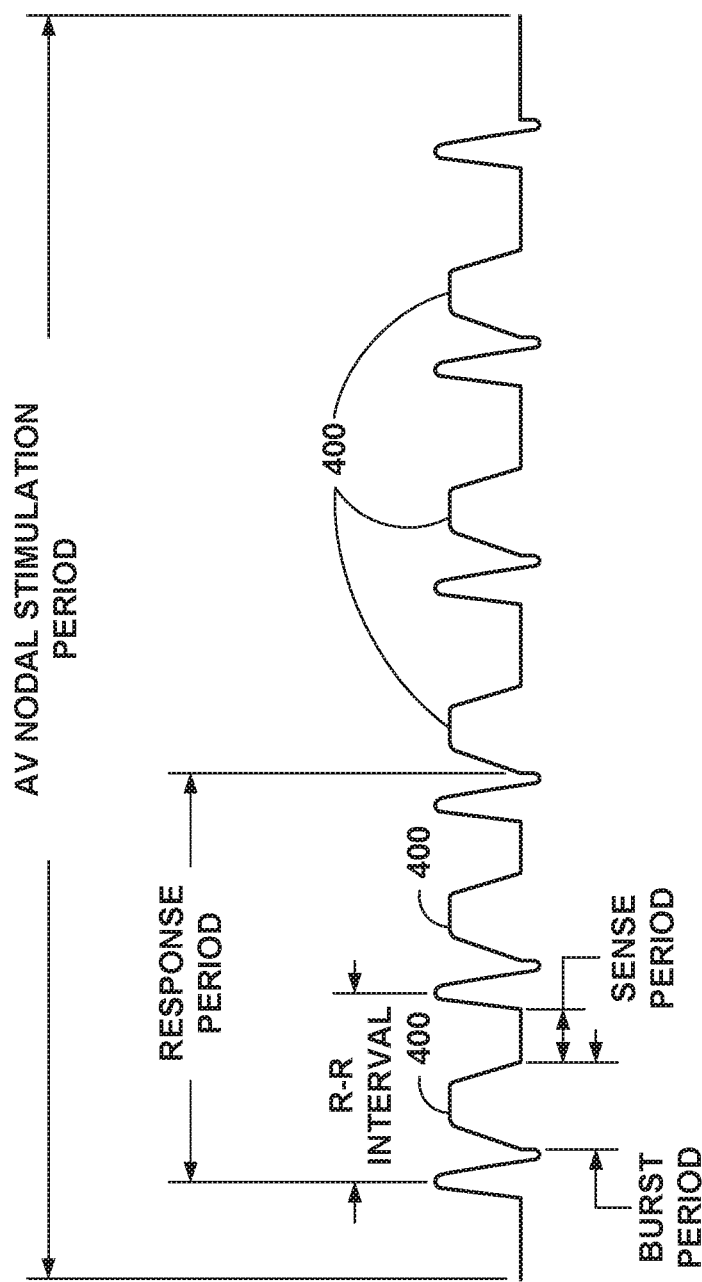
FIG. 9 is a graph illustrating a series of vagal stimulation bursts delivered over the course of a number of depolarizations and repolarizations of the heart of a patient.

Once the response time period has ended (306), or some other allowable time period over which violation of a threshold sense time period is acceptable, however, processor 80 may thereafter control signal generator 84 to deliver AV nodal, e.g. vagal stimulation to patient 14 based on the determined sense time period (308). In one example, processor 80 controls signal generator 84 to deliver stimulation in the form of bursts, pulses, or trains of pulses such that each such stimulation occurrence, e.g. one burst occurs of a time period that does not exceed approximately 50% of the median R-R interval, which, in turn, permits sensing module 86 to sense ventricular depolarizations over a sense time period equal to at least approximately 50% of the median R-R interval. FIG. 9 is a graph illustrating the median R-R interval for heart 12 of patient 14 and the delivery of AV nodal stimulation in accordance with the example of FIG. 8 by first delivering stimulation regardless of a measured sense time period (304), and, once a stimulation response period has ended (306), delivering stimulation to the patient based on the determined sense time period (308).

In FIG. 9, processor 80 controls signal generator 84 to deliver a series of, e.g. AV nodal vagal stimulation bursts 400 to heart 12 of patient 14 over a total stimulation time period. Upon initiating vagal stimulation before a stimulation response time period ends, processor 80 controls signal generator 84 to deliver vagal stimulation regardless of the quantity of the sense time period over which it is possible for sensing module 86 to sense ventricular depolarizations, e.g. for the purposes of detecting a serious arrhythmia in ventricles 28, 32, e.g. ventricular fibrillation. As such, as illustrated in the example of FIG. 9, processor 80 may control signal generator 84 to deliver vagal stimulation before the response time period ends even though the stimulation burst time period is more than approximately 50% of the median R-R interval, which limits the sense time period to less than the threshold approximately 50% of the median R-R interval. After the stimulation response time period ends, processor 80 may thereafter control signal generator 84 to deliver vagal stimulation based on a target sense time period, e.g. a sense time period greater than or equal to approximately 50% of the median R-R interval. As such, as illustrated in FIG. 9, after the stimulation response time period ends, the burst time period for bursts delivered by signal generator 80 may be less than or equal to approximately 50% of the median R-R interval, which will permit the sense time period to be greater than or equal to the threshold approximately 50% of the median R-R interval.

Although the example of FIG. 9 is illustrated in terms of sense time periods for a single burst cycle of vagal stimulation between successive ventricular depolarizations, as noted above, in some examples, the threshold for the sense time period may be a percentage of the total stimulation time period such that the accumulation of blanking periods during the total stimulation time period does not exceed the threshold percentage. In one example, the threshold is 50% such that during 30 seconds of vagal stimulation a window of at least 15 seconds in which sensing module 86 may sense activity in ventricles 28, 32 is needed.

Referring again to the example method of FIG. 8, in some examples, IMD 16 may be configured to synchronize the delivery of AV nodal stimulation with a QRS complex of heart 12. In particular, IMD 16 may be configured to deliver the vagal stimulation in a refractory period between depolarization/repolarization cycles. During the refractory period, the stimulation is less likely to depolarize heart 12, and, in particular, ventricles 28, 32.

IMD 16 continues to deliver AV nodal stimulation until one or more stimulation termination criteria are satisfied (240), at which point the device terminates the stimulation (242). In one example, the termination criteria includes at least one of expiration of a programmed stimulation delivery time period, an accumulation of blanking time periods that exceeds a threshold percentage of a stimulation delivery time period, failure to detect a threshold ventricular rate response within a stimulation response time period, or detection of a ventricular tachyarrhythmia.

In some examples, IMD 16 is programmed, e.g. according to a therapy program stored in memory 82 to deliver AV nodal vagal stimulation for a specific period of time. The programmed stimulation time period may be set to a value that provides a sufficient amount of time for IMD 16 to test the effectiveness of the stimulation in modulating the ventricular rate response. Additionally, regardless of other termination criteria, the stimulation time period may be set to a value that provides hysteresis such that IMD 16 is not rapidly toggling between turning vagal stimulation on and off. In one example, processor 80 of IMD 16 is programmed with a vagal stimulation time period stored in memory 82 in a range from approximately 20 seconds to approximately 30 seconds, upon the expiration of which processor 80 is programmed to terminate delivery of vagal stimulation to heart 12 of patient 14 (242).

In one example, processor 80 may be programmed to control sensing module 86 to monitor the stimulation delivered by signal generator 84 and the periods of time sensing module 86 is sensing activity in ventricles 28, 32 during stimulation to ensure that an accumulated blanking period does not exceed a threshold percentage of a stimulation delivery time period stored in memory 82. In the event the blanking periods exceed a threshold, which corresponds to a sense time period being less than a threshold, processor 80 may be programmed to control signal generator 84 to terminate stimulation. In some examples, however, processor 80 may be programmed to allow the blanking period, which may generally correspond to the stimulation burst period to exceed a threshold percentage of the contraction frequency in ventricles 28, 32 for a brief period at the beginning of the delivery of AV nodal stimulation before the effect of the stimulation is able to slow the contractions of ventricles 28, 32.

In addition to stimulation time period expiration and blanking period accumulation, processor 80 may be programmed to control signal generator 84 to terminate the delivery of AV nodal stimulation (242) in the event a minimum ventricular rate response is not observed within a programmed response time period. In one example, processor 80 may be programmed to terminate AV nodal vagal stimulation if the contraction rate of ventricles 28, 32 does not decrease by a threshold amount within the stimulation response time period. The minimum ventricular rate response may differ from one patient to another and may be set as a relative percentage reduction or as an absolute value rate reduction. In examples in which the minimum rate response is set as an absolute value, the value by which processor 80 measures rate response may be tiered depending on the observed contraction rate of ventricles 28, 32, i.e. the minimum rate response may be higher for higher initial ventricular contraction rates and lower for lower ventricular contraction rates.

In one example, processor 80 is programmed with a vagal stimulation response time period of approximately 10 seconds or in a range of 5 to 10 beats of heart 12. Additionally, processor 80 is programmed with a minimum rate response approximately equal to a 20% rate reduction from the initial contraction rate of ventricles 28, 32 measured by sensing module 86. In another example, IMD 16 is programmed with a minimum rate response approximately equal to 40 bpm for higher initial ventricular contraction rates on the order of 180 bpm or higher, and a minimum rate response approximately equal to 20 bpm for lower initial ventricular contraction rates on the order of 120 bpm or lower. The stimulation response time period and minimum ventricular rate response values, which are employed by processor 80 as basis for controlling signal generator 84 to terminate stimulation (242), may, in some examples, be stored in memory 82 of IMD 16.

Various examples have been described that include providing AV nodal stimulation during atrial tachyarrhythmia to control ventricular rate response and thereby prevent ventricular tachyarrhythmia misdiagnosis and treatment delivery. In one example, AV nodal vagal stimulation may include stimulation of the AV nodal region of a patient's heart through, e.g., a single endocardial screw-in lead that provides atrial pacing/sensing as well as the AV nodal vagal stimulation. While the foregoing examples are described with reference to preventing or reducing the risk of delivering inappropriate shocks to a patient, there are a number of other applications for examples according to this disclosure. First, by better controlling the ventricular rate during AF, patient symptoms may be reduced. Secondly, by preventing rapidly conducted AF, it may be possible to deliver a greater percentage of bi-ventricular pacing therapy to CRT patients. These and other examples are within the scope of the following claims.

The invention claimed is:
1. A system comprising:
 a stimulation generator configured to deliver electrical stimulation to a patient;

a sensing module configured to sense activity of the patient's heart; and a processor coupled to the sensing module and configured to:

anticipate a ventricular tachyarrhythmia in a heart of a patient based on the ventricular tachyarrhythmia not yet being detected but a counter reaching a threshold value of a ventricular tachyarrhythmia event count;

determine a sense time period; and in response to anticipating the ventricular tachyarrhythmia, control the stimulation generator to deliver electrical stimulation to block the atrioventricular node of the heart over an electrical stimulation delivery time period, wherein the electrical stimulation delivery time period is based on the sense time period over which ventricular depolarizations can be sensed during the electrical stimulation delivery time period, the electrical stimulation delivery time period being bounded by limits that prevent an accumulation of blanking periods applied to a sensing amplifier that would exceed the sense time period.

2. The system of claim 1, wherein the processor is configured to detect an atrial tachyarrhythmia, and anticipate, during the detected atrial tachyarrhythmia, detection of the ventricular tachyarrhythmia in the heart of the patient based on the ventricular tachyarrhythmia not yet being detected but the counter reaching the threshold value of the ventricular tachyarrhythmia event count.

3. The system of claim 1, wherein the processor is configured to detect an atrial tachyarrhythmia comprising at least one of atrial fibrillation or atrial tachycardia.

4. The system of claim 3, wherein the processor detecting the atrial tachyarrhythmia comprises:

detecting a P-P interval value for the heart of the patient that is less than a percentage threshold of an R-R interval value; and analyzing a rhythm of the heart of the patient for indications of sinus tachycardia.

5. The system of claim 1, wherein the processor is configured to anticipate a ventricular tachyarrhythmia based at least on the threshold value of the ventricular tachyarrhythmia event count.

6. The system of claim 5, wherein the ventricular tachyarrhythmia event count comprises a number of sensed ventricular intervals indicative of the ventricular tachyarrhythmia.

7. The system of claim 1, wherein the processor is configured to control the stimulation generator to deliver the electrical stimulation during a refractory period of the heart of the patient.

8. The system of claim 1, wherein the processor is configured confirm, prior to controlling the stimulation generator to deliver the electrical stimulation, that a median RR interval for the heart of the patient is less than a maximum threshold ventricular contraction rate and greater than or equal to a minimum threshold ventricular contraction rate.

9. The system of claim 1, wherein the processor is configured to determine the sense time period based on an R-R interval of the heart of the patient.

10. The system of claim 9, wherein the processor determining the sense time period based on an R-R interval of the heart of the patient comprises:

measuring a plurality of R-R intervals for the heart of the patient;

calculating a median R-R interval from the measured R-R intervals; and setting the sense time period to greater than or equal to a predetermined portion of the median R-R interval.

11. The system of claim 1, wherein the processor is configured to control the stimulation generator to terminate the delivery of electrical stimulation based on one or more stimulation termination criteria, wherein the one or more stimulation termination criteria comprises at least one of expiration of an electrical stimulation delivery time period, an accumulation of blanking time periods exceeding a threshold percentage of the electrical stimulation delivery time period, failure to detect a threshold ventricular rate response within an electrical stimulation response time period, or detection of a ventricular tachyarrhythmia.

12. The system of claim 9, wherein the processor determining the sense time period using on an R-R interval comprises:

measuring a plurality of R-R intervals for the heart of the patient;

calculating a median R-R interval from the measured R-R intervals; and setting the sense time period to greater than or equal to a predetermined portion of the median R-R interval.

13. A system comprising:

a stimulation generator configured to deliver electrical stimulation to a patient; and a processor configured to:

increment a counter upon detection of a ventricular tachyarrhythmia event;

anticipate detection of a ventricular tachyarrhythmia in a heart of a patient based on the ventricular tachyarrhythmia not yet being detected but a counter reaching a threshold value of a ventricular tachyarrhythmia event count;

measure an RR interval;

determine, using the RR interval, a sense time period over which ventricular depolarizations need to be sensed in order to detect development of the ventricular tachyarrhythmia;

determine a stimulation time period based on the sense time period;

in response to anticipating detection of the ventricular tachyarrhythmia, control the stimulation generator to deliver electrical stimulation to block an atrioventricular node of the heart over a first time period regardless of the sense time period; and control the stimulation generator to deliver the electrical stimulation during the stimulation time period over a second time period after the first time period, the stimulation time period being bounded by limits that prevent an accumulation of blanking periods applied to a sensing amplifier that would exceed the sense time period.

14. The system of claim 13, wherein the processor is configured to detect an atrial tachyarrhythmia, and anticipate during the detected atrial tachyarrhythmia, detection of the ventricular tachyarrhythmia in the heart of the patient based on the ventricular tachyarrhythmia not yet being detected but the counter reaching the threshold value of the ventricular tachyarrhythmia event count.

15. The system of claim 13, wherein the processor is configured to detect an atrial tachyarrhythmia comprising at least one of atrial fibrillation or atrial tachycardia.

16. The system of claim 15, wherein the processor detecting the atrial tachyarrhythmia comprises:

detecting a P-P interval value for the heart of the patient that is less than a percentage threshold of an R-R interval value; and analyzing a rhythm of the heart of the patient for indications of sinus tachycardia.

17. The system of claim 13, wherein the processor is configured to anticipate a ventricular tachyarrhythmia based at least on the threshold value of the ventricular tachyarrhythmia event count, and wherein the ventricular tachyarrhythmia event count comprises a number of sensed ventricular intervals indicative of the ventricular tachyarrhythmia.

18. The system of claim 13, wherein the processor is configured to control the stimulation generator to deliver the electrical stimulation during a refractory period of the heart of the patient.

19. The system of claim 13, wherein the processor is configured confirm, prior to controlling the stimulation generator to deliver the electrical stimulation, that a median RR interval for the heart of the patient is less than a maximum threshold ventricular contraction rate and greater than or equal to a minimum threshold ventricular contraction rate.

20. The system of claim 13, wherein the processor is configured to control the stimulation generator to terminate the delivery of electrical stimulation based on one or more stimulation termination criteria, wherein the one or more stimulation termination criteria comprises at least one of expiration of an electrical stimulation delivery time period, an accumulation of blanking time periods exceeding a threshold percentage of the electrical stimulation delivery time period, failure to detect a threshold ventricular rate response within an electrical stimulation response time period, or detection of a ventricular tachyarrhythmia.

* * * * *